(12) United States Patent
Magnin et al.

(10) Patent No.: US 8,007,440 B2
(45) Date of Patent: Aug. 30, 2011

(54) APPARATUS AND METHODS FOR LOW-COST INTRAVASCULAR ULTRASOUND IMAGING AND FOR CROSSING SEVERE VASCULAR OCCLUSIONS

(75) Inventors: Paul A. Magnin, Andover, MA (US); Edward I. McNamara, Chelmsford, MA (US); Russell W. Bowden, Tyngsboro, MA (US); Rodney J. Solomon, Lowell, MA (US)

(73) Assignee: Volcano Corporation, San Diego, CA (US)

( * ) Notice: Subject to any disclaimer, the term of this patent is extended or adjusted under 35 U.S.C. 154(b) by 1404 days.

(21) Appl. No.: 11/053,141

(22) Filed: Feb. 8, 2005

(65) Prior Publication Data

US 2008/0146918 A1    Jun. 19, 2008

(51) Int. Cl.
*A61B 8/14* (2006.01)

(52) U.S. Cl. ........ 600/467; 600/437; 600/439; 600/462; 600/463; 600/466

(58) Field of Classification Search ........................ None
See application file for complete search history.

(56) References Cited

U.S. PATENT DOCUMENTS

| | | | |
|---|---|---|---|
| 2,056,377 A | 10/1936 | Wappler | |
| 4,532,924 A | 8/1985 | Auth et al. | |
| 4,643,186 A | 2/1987 | Rosen et al. | |
| 4,682,596 A | 7/1987 | Bales et al. | |
| 4,794,931 A | 1/1989 | Yock | |
| 4,951,677 A * | 8/1990 | Crowley et al. | 600/463 |
| 5,000,185 A | 3/1991 | Yock | |
| 5,109,859 A | 5/1992 | Jenkins | |
| 5,243,988 A | 9/1993 | Sieben et al. | |
| 5,313,949 A | 5/1994 | Yock | |
| 5,345,940 A | 9/1994 | Seward et al. | |
| 5,350,390 A | 9/1994 | Sher | |

(Continued)

FOREIGN PATENT DOCUMENTS

NL    8700632    10/1988

OTHER PUBLICATIONS

Slager, et al., "Directional Plaque Ablation by Spark Erosion Under Ultrasound Guidance: First Evaluation of a Catheter Incorporating Both Techniques", Chapter 8, pp. 81-90, part of a Thesis book that was published Dec. 17, 1997 at a public presentation.

(Continued)

*Primary Examiner* — Unsu Jung
*Assistant Examiner* — Nigel Fontenot
(74) *Attorney, Agent, or Firm* — Haynes and Boone, LLP

(57) ABSTRACT

An intravascular ultrasound catheter system is provided and enables a simplified, economical technique for ultrasound visualization of a blood vessel. The catheter may include a spark ablation system for crossing chronic total occlusions and severe stenoses. The catheter is advanceable and is oriented entirely under manual control of the clinician and the application of radiofrequency energy for spark erosion of the stenosis also is controlled manually by the clinician. The system enables the clinician to observe an ultrasound image sufficiently to determine where to orient the ablation electrode so as to reduce the risk of dissection or perforation of the blood vessel. The ultrasound image is generated in response to manual rotation of the catheter and the ablation spark is generated only when the physician is satisfied as to the orientation of the electrode within the vessel.

47 Claims, 15 Drawing Sheets

U.S. PATENT DOCUMENTS

| | | | |
|---|---|---|---|
| 5,366,443 | A | 11/1994 | Eggers et al. |
| 5,373,845 | A | 12/1994 | Gardineer et al. |
| 5,421,338 | A | 6/1995 | Crowley et al. |
| 5,454,809 | A | 10/1995 | Janssen |
| 5,577,506 | A | 11/1996 | Dias |
| 5,588,432 | A | 12/1996 | Crowley |
| 5,606,975 | A | 3/1997 | Liang et al. |
| 5,651,366 | A | 7/1997 | Liang et al. |
| 5,697,909 | A | 12/1997 | Eggers et al. |
| 5,741,270 | A | 4/1998 | Hansen et al. |
| 5,749,914 | A | 5/1998 | Janssen |
| 5,840,030 | A * | 11/1998 | Ferek-Petric et al. ........ 600/439 |
| 5,935,108 | A | 8/1999 | Katoh et al. |
| 6,200,269 | B1 | 3/2001 | Lin et al. |
| 6,241,744 | B1 * | 6/2001 | Imran et al. .................. 606/159 |
| 6,394,956 | B1 | 5/2002 | Chandrasekaran et al. |
| 6,461,383 | B1 | 10/2002 | Gesswein et al. |
| 6,638,222 | B2 | 10/2003 | Chandrasekaran et al. |
| 2002/0032437 | A1 | 3/2002 | Andrews et al. |
| 2002/0183826 | A1 | 12/2002 | Dorn et al. |
| 2003/0040737 | A1 * | 2/2003 | Merril et al. ...................... 606/1 |
| 2004/0015065 | A1 | 1/2004 | Panescu et al. |

OTHER PUBLICATIONS

Slager, et al., "Spark Erosion and Its Combination with Sensing Devices for Ablation of Vascular Lesions", Chapter 13, in John H.K. Vogel and Spencer B. King, III, *Interventional Cardiology: Future Directions*, The C.V. Mosby Company, St. Louis, 1989, pp. 157-169.

Slager, et al., "Vaporization of Atherosclerotic Plaques by Spark Erosion," *J Am Coll Cardiol*, 1985, 5:1382-6.

* cited by examiner

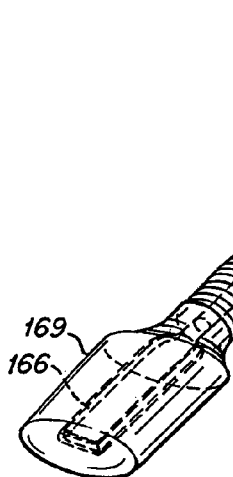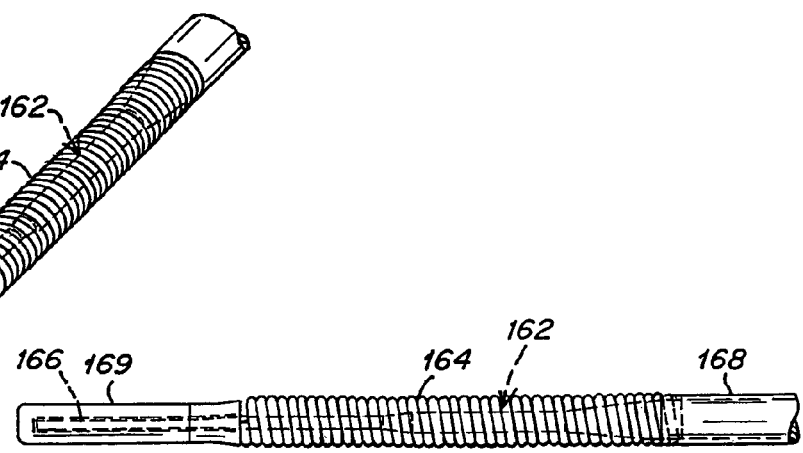
Fig. 18A    Fig. 18B
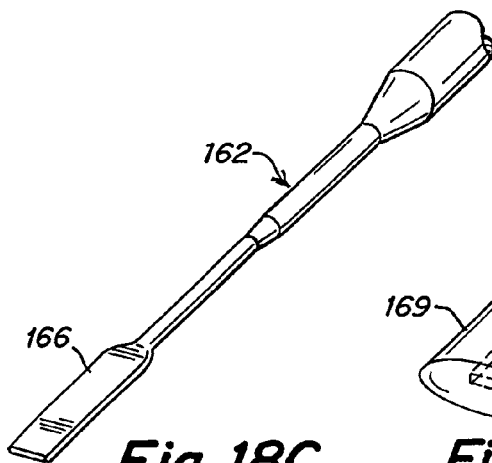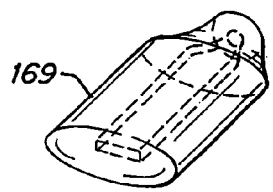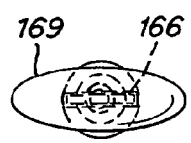
Fig. 18C    Fig. 18D    Fig. 18E
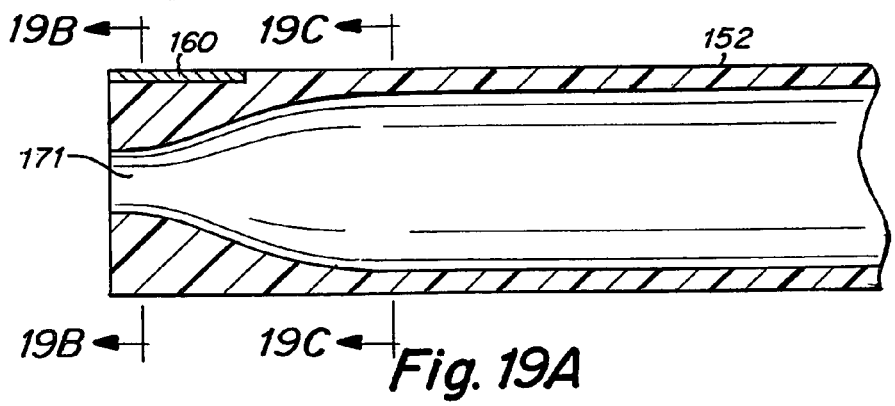
Fig. 19A
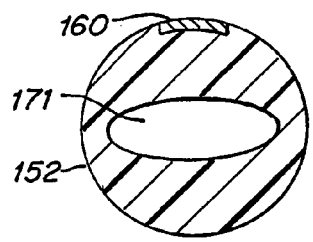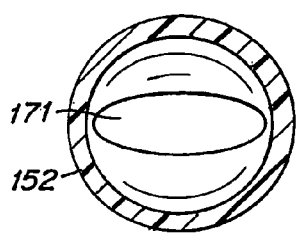
Fig. 19B    Fig. 19C

APPARATUS AND METHODS FOR LOW-COST INTRAVASCULAR ULTRASOUND IMAGING AND FOR CROSSING SEVERE VASCULAR OCCLUSIONS

FIELD OF THE INVENTION

The invention relates to medical devices and techniques by which an effectively total occlusion in a blood vessel, such as a chronic total occlusion, an acute total occlusion or a severe stenosis, may be penetrated sufficiently to enable treatment of the stenosis with intravascular treatment devices and techniques.

BACKGROUND

Before the development of less invasive approaches, the principal mode of treatment for occluded arteries was bypass surgery and, in the case of occlusions in the coronary arteries, coronary artery bypass surgery. Coronary artery bypass surgery is a highly invasive procedure in which the chest cavity is opened to expose the heart to provide direct surgical access to the coronary arteries. The procedure also includes the surgical removal of blood vessels from other locations in the patient's body (e.g., the saphenous vein) which then are grafted surgically to the coronary arteries to bypass the occlusions. The recuperative period is lengthy with considerable discomfort to the patient.

The use of less invasive, catheter-based, intravascular techniques has developed for several decades and may be considered as the preferred mode of treatment for those patients amenable to such treatment. Typically, the intravascular procedures, such as angioplasty, atherectomy, and stenting require preliminary navigation of a guidewire through the patient's arteries to and through the occlusion. This guidewire, so placed, serves as a rail along which catheters can be advanced directly to and withdrawn from the target site. Total occlusions often cannot be treated with such minimally invasive intravascular approaches because of the inability to advance a guidewire through the stenosis. Typically patients with such occlusions have been treatable, if at all, by pass surgery. Although in some instances, the physician may be able to force a guidewire through a total occlusion if the occluding material is relatively soft, that may present serious risks of perforating the artery. Arterial perforation can be life threatening.

The difficulties presented when trying to cross a total or near-total occlusion are compounded by the typical manner in which the anatomy of an occluded artery is diagnosed. Conventionally, such diagnosis involves an angiographic procedure in which a radiopaque contrast liquid is injected into the artery upstream of the occlusion and a radiographic image is made. The resulting image is that of the compromised lumen which necessarily differs from the natural arterial lumen. Although with angiographic visualization techniques, the physician can determine the location of the occluded region and an indication of the degree of obstruction, angiographic images do not provide a clear understanding of where, in the occluded region, the natural boundaries of the vessel are located.

As used herein, the term "severe occlusion" or "severe obstruction" is intended to include total occlusions as well as those occlusions and stenoses that are so restrictive as to require preliminary formation of a passage through the occlusion in order to receive additional intravascular therapeutic devices. Such occlusions may have various causes and may occur in the arterial or venous systems. Total or near total occlusions may occur as a consequence of the build-up of plaque or thrombus, the latter being problematic in arteries as well as in the venous system. For example, deep veined thrombus and thrombotic occlusion of vein grafts are serious conditions requiring treatment.

More recently, techniques and systems have been developed to visualize the anatomy of vascular occlusions by using intravascular ultrasound (IVUS) imaging. IVUS techniques are catheter-based and provide a real-time sectional image of the arterial lumen and the arterial wall. An IVUS catheter includes one or more ultrasound transducers at the tip of the catheter by which images containing cross-sectional information of the artery under investigation can be determined. IVUS imaging permits visualization of the configuration of the obstructing material and, in varying degrees, the boundaries of the intimal and medial layers of the arterial wall. One common type of IVUS imaging catheter system typically includes an arrangement in which a single transducer at the distal end of the catheter is rotated at high speed (up to about 2000 rpm) to generate a rapid series of 360-degree ultrasound sweeps. Such speeds result in generation of up to about thirty images per second, effectively presenting a real-time sectional image of the diseased artery. The transducer is mounted on the end of a drive shaft that is connected to a motor drive at the proximal end of the catheter. The rotating transducer is housed in a sheath that does not interfere with the ultrasound and protects the artery from the rapidly spinning drive shaft. Thus, an IVUS imaging catheter may be advanced to the region of an occlusion using conventional angiographic techniques and then may be operated to provide real-time sectional images of the vascular lumen in the arterial wall, including the occluding material and intimal and medial layers of the artery wall.

Proposals and development efforts have been made to combine IVUS imaging techniques with a catheter adapted to remove obstructive material from the artery. One such arrangement has been to provide a catheter having spark erosion electrodes by which obstructive plaque can be ablated in conjunction with an IVUS imaging system by which the anatomy of the artery and obstruction may be visualized. The objective of such catheters is to provide the physician with information as to the location and the characteristics of the stenosis, coupled with the ability to provide a controlled spark erosion of the occlusive materials. Ideally, the system should remove only plaque deposited on the inner luminal surface of the artery and in the innermost intimal layer which, typically, will have been thickened, often irregularly, as a consequence of the plaque deposits. Typically, there is little development of plaque within the medial layers of the artery. The system desirably should have the ability to remove plaque-laden intima without causing dissections, releasing obstructive material into the bloodstream or provoking other major adverse side effects.

Such systems are described, for example, in Slager, et al., Directional Plaque Ablation by Spark Erosion Under Ultrasound Guidance: First Evaluation of a Catheter Incorporating Both Techniques, Dissertation Public Presentation Dec. 17, 1997, and included as Chapter 8 in Slager, Cornelis Jacob, "Removal of Cardiovascular Obstructions by Spark Erosion", ISBN 90-9011073-9, printed by ICG Printing Dordrecht. The system is described as including a catheter adapted to contain a stainless steel tubular rotatable drive shaft. A tip, mounted at the distal end of the drive shaft, includes a circular ultrasound transducer and a sparking electrode. Wires for the ultrasound signals and a high-voltage wire to transmit RF energy to the active electrode extend through the lumen in the drive shaft. A slip ring construction near the proximal end of the drive shaft provides electrical connection between the electrode wire and the spark erosion generator. The proximal end of the drive shaft is connected to a motor drive unit. The drive shaft is selected to be torsionally stiff to synchronize the angular orientation of the tip and the motor drive unit. The device is operated at a tip rotation frequency of 12.5 Hz (750 rpm). Timing of the start of the spark erosion pulse is described as related to the timing signals obtained from the ultrasound imaging equipment. Another such system is described in U.S. Pat. No. 6,394,956 which also describes a catheter having a drive shaft that rotates an ultrasound transducer and electrode at a rate of approximately 1500 to 2000 rpm. These RF ablation systems using IVUS imaging are intended to image, in real time, at about twelve to about thirty image frames per second. They tend to be very expensive systems due to the complexity of the real time electronics and related mechanical features.

It would be desirable to provide a low cost, simplified, intravascular ultrasound system and to provide such a system to guide a therapeutic device for the treatment for total vascular occlusions and it is among the general objects of the present invention to provide such systems and techniques.

SUMMARY

The invention relates to devices and techniques for IVUS imaging in a low cost system and for combining such low-cost IVUS imaging with RF ablation adapted to facilitate crossing of total or severe vascular occlusions sufficiently to enable an intravascular device, such as a guidewire and subsequently placed therapeutic device, to pass through the occlusion. In accordance with the invention, the distal tip of an intravascularly-inserted IVUS device is caused to rotate and to be advanced along the vessel entirely and solely under the manual control of the physician. In one aspect, the tip includes an ultrasound transducer and one or more ablation electrodes. The angular positions of the tip and the electrode are monitored by an angle encoder attached to the proximal portion of the rotatable shaft of the catheter that is disposed outside of the patient. The angle encoder provides angular positional information while the ultrasound signals generate echo information from which a sectional image of the vascular anatomy can be displayed on an imaging system in sufficient detail to enable sectional visualization of the vessel wall. In particular, the system enables visualization of the intimal and medial layers of an artery, or the anatomy of an obstructed vein sufficiently to permit the ablation electrode to be steered and positioned safely within the approximate bounds of the natural lumen while advancing across the obstruction. The risk of perforation and dissection of the vessel wall is significantly reduced.

The ultrasonic transducer is electrically connected to an imaging system and a monitor so that the operator can observe the progress of the distal end of the device through the artery and, in particular, the proximity of the ablation electrode to the medial layers of the artery or the venous structure. By visualizing these structures prior to each application of RF energy, the operator can position manually the ablation electrode to avoid ablation of the native vessel wall structure. The application of an ablation spark is controlled manually by the operator after the operator has determined that the electrode is oriented in the desired position within the vessel. Thus, the system allows the ablation path through the occlusion to be controlled by the operator by steering the distal tip of the catheter away from the boundary of the native vessel wall and performing ablation at a location that is safely spaced from that boundary.

The invention achieves these objectives with a system that is greatly simplified as compared to those of the prior art. In particular, the invention omits the use of a rapidly spinning imaging core and departs from the prior art approach of providing a rapidly presented real-time stream of images. It also omits the use of timing systems for activating the ablation electrode at the precisely correct rotational position of the rapidly spinning shaft. Instead, the ultrasonic guidance systems of the invention provide an ultrasound image of the vessel only intermittently, but with sufficient frequency to enable the physician to position and ablate a precisely selected portion of the obstruction at a safe and satisfactory rate. The device is manipulated by the physician to rotate gently the distal tip of the catheter within the vessel and the ultrasound transducer operates in response to and during such manual rotation. The physician can obtain sufficient imaging of the vessel to determine its wall structure by rotating the catheter tip through part of or, at most, a few revolutions. Rotation can be clockwise or counter-clockwise at the user's discretion. The invention avoids the need to protect against injury to the vessel wall from a rapidly-spinning imaging core. Additionally, there is no need for electronic slip rings, transformer couplings or other sliding electrical contacts between a continually rotating transducer and a stationary electronics module.

The electronics module includes circuitry that generates the energy to create the ultrasonic pulse and to send the collected reflection data to a central processor where it is reconstructed into an image of the vessel. The images are displayed and updated each time the catheter is rotated. The circuitry may be controlled by software to include a persistence function by which the image begins to fade after a predetermined time in order to encourage the operator to update the image information with sufficiency frequency to prevent reliance on older, possibly less accurate, image information.

In another aspect of the invention, the catheter is configured to facilitate advancement of its distal tip into the cavity created during the RF ablation. In some embodiments, the design may include specially formed surfaces on the distal tip to guide the distal tip into the cavity in response to distal advancement of the catheter.

In another embodiment incorporating the principles of the invention, the catheter may include a guidewire that extends through a lumen in the catheter and is keyed to the catheter to prevent relative rotation of the guidewire and catheter. In this embodiment, the distal end of the guidewire is formed to assume a predetermined curve when in its relaxed configuration such that it will assume that curve when it is extended out of the distal end of the catheter. The guidewire can be withdrawn fully into the catheter. In this embodiment of the invention, the tip of the catheter includes an RF ablation electrode oriented to lie along the same plane as that defined by the curve of the distal end of the guidewire. Thus, after the RF ablation electrode has been activated to ablate a portion of the arterial obstruction, the guidewire can be projected forwardly, progressively assuming its curved configuration as it emerges from the distal tip of the catheter. In so doing, the distal tip of the guidewire is advanced into the ablated cavity. The catheter then can be advanced along the guidewire to guide its tip into the cavity in readiness for another cycle.

In another aspect, the intravascular ultrasound system may be used independently of an ablation device where it is desirable to have a low-cost, easily used arrangement for observing, intravascularly, the anatomy of a vessel wall. These and other aspects of the invention are explained further in the following descriptions.

BRIEF DESCRIPTION OF THE DRAWINGS

The foregoing and other objects, advantages and principles of the invention will be appreciated more fully from the following further description thereof, with reference to the accompanying drawings, generally not to scale, wherein:

FIG. 17-B is a diagrammatic illustration of the catheter of FIG. 17-A with its tip advanced up to the proximal surface of a total occlusion;

FIG. 17-C is a diagrammatic illustration of the activation of the RF ablation energy and the subsequent ablation of the tissue surrounding the RF antenna;

FIG. 17-D is a diagrammatic illustration of the guidewire exiting the distal end of the catheter and entering the RF-created void;

FIG. 17-E is an illustration of the catheter being advanced over the previously extended guidewire to follow it into the void to guide the distal end of the catheter into the ablated void;

FIGS. 18A and 18B are illustrations of the distal portion of a guidewire as may be employed in the embodiment of FIG. 17A;

FIG. 18C is an illustration of the distal region of the core wire of the guidewire of FIGS. 18A and 18B;

FIG. 18D is an illustration of a shaped tip cover for the distal end of the core wire;

FIG. 18E is an end view of the device of FIG. 18B;

FIG. 19A is a longitudinal sectional illustration of the distal portion of a catheter of the type shown in FIG. 17A;

FIG. 19B is a sectional illustration of the catheter of FIG. 19A as seen along line 19B-19B of FIG. 19A;

FIG. 19C is a sectional illustration of the catheter of FIG. 19A as seen along the line 19C-19C.

DETAILED DESCRIPTION

Figure 1:
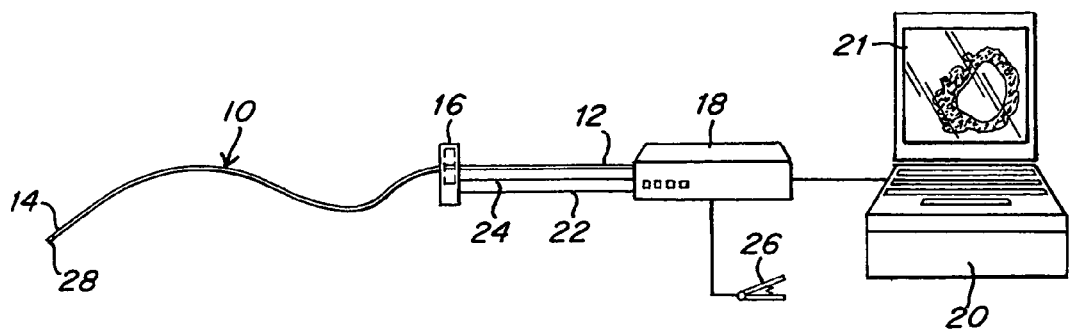
FIG. 1 illustrates the general relationship of components in a preferred embodiment of the system.

FIG. 1 illustrates, generally, the components of a preferred embodiment of the invention. The system includes a catheter 10, having proximal and distal ends 12, 14. The distal end 14 is adapted to be inserted into the patient and is constructed to be navigable through the patient's vasculature to advance the distal tip of the catheter to the intended treatment site. The catheter includes a distal tip that carries an ultrasound transducer and an ablation electrode adapted to ablate an obstructed portion of the vessel. The proximal end 12 remains outside of the patient where it can be associated with an angle encoder 16 and can be manipulated by the physician. The system includes an electronics module 18 that includes circuitry and software for generating signals for operating the ultrasonic system and for receiving and processing the signals from resulting ultrasound echoes, as well as for generating the RF ablation signal. The central processing unit 20 constructs the images from the received ultrasound signals and displays the image on a monitor 21. The image is generated on demand and is refreshed in response to operator rotation of the catheter. The image may be caused to fade after a predetermined time as a reminder to the operator to refresh the image by rotating the catheter. The central processing unit 20 may comprise a laptop or desktop computer or a dedicated embedded processor. Cables 22, 24 are connected between the angle encoder 16 and electronics module 18. One cable 22 carries the incremental angle information that is sensed by the angle encoder 16 and the other cable 24 provides power and ground. Separate cables run from the catheter to the electronics module 18 and carry ultrasound signals and RF energy. In an alternate arrangement (not shown), the transducer and RF cables from the catheter could plug into a connector integrated into the angle encoder and then, after possibly preamplifying the ultrasound signals, pass the signal through a second connector on the angle encoder to the electronics module 18. This alternate arrangement would allow for a shorter catheter cable and, potentially, reduce environmental noise pick-up.

Among the features of the invention is that the catheter is rotated and manipulated entirely under the manual control of the physician. Similarly, the initiation of the ablation pulse is determined by the physician independently of any direct connection with the catheter or the system for sensing catheter rotation. It should be understood, however, that reference to "manual" with respect to control over the application of ablation energy may include any arrangement by which the physician, based on judgment as to the proper location of the ablation electrode, initiates the ablation sequence. Thus, "manual" operation may include a variety of arrangements, including, mechanically controlled switches (e.g., a foot switch, or a voice-operated control) or other means by which the physician can trigger the ablation cycle.

Figure 2:
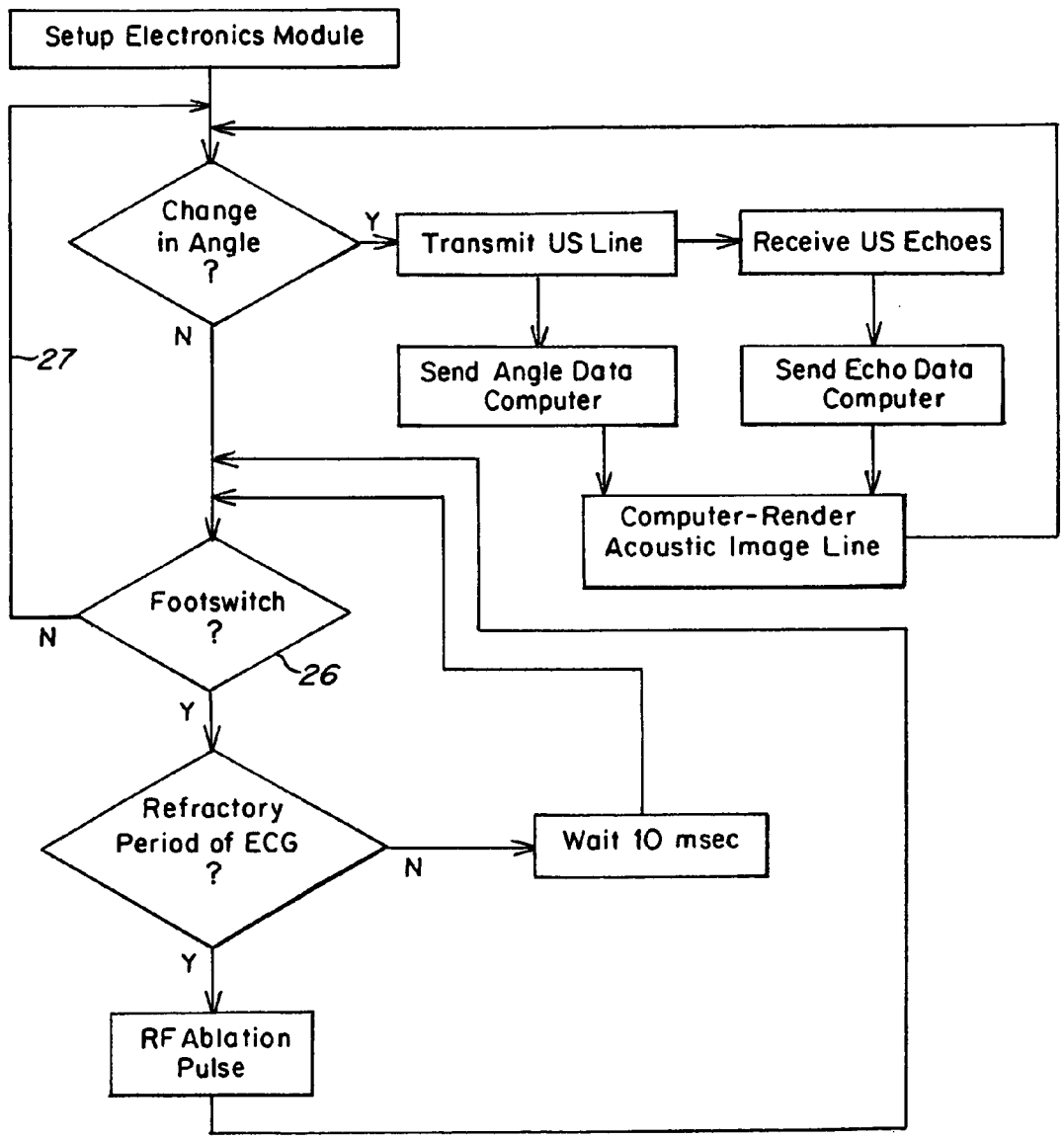
FIG. 2 is a diagram illustrating the functioning and operational sequence of elements of the electronics module.

FIG. 2 is a diagram illustrating the functioning of the electronics module 18. Module 18 receives inputs from the angle encoder 16 and from an operator controlled foot switch 26. All of the set-up for the electronics and all of the output of the electronics module is done by a central processor, such as a laptop computer. When the system is turned on, the computer loads the appropriate default parameters into the electronics module and the system enters a quiescent state awaiting detection of an angle change from the angle encoder or a command from the foot switch. If an angle change has been sensed by the angle encoder, the electronics module energizes the ultrasound transducer and then it receives the resultant echoes. The echo information along with the angle information is sent to the computer where it is rendered into a sectional image of the artery. This continues until the angle encoder 16 ceases to register changes. When the foot switch is pressed, the system, which also includes an input from ECG attached to the patient, senses the patient's ECG signal to determine if the patient's heart is in the refractory period of the heart cycle and, if so, an RF pulse or pulse train is emitted to cause ablation of occlusive tissue. The system then, again, interrogates whether the foot switch is on and, if so, it repeats the loop. If the switch is off, then the quiescent loop 27 is entered until the next input from either the foot switch or the angle encoder is sensed.

The catheter shaft may be made by any of a variety of construction techniques, well known to those familiar with catheter design, adapted to provide a desired balance between longitudinal flexibility and torsional stiffness. The longitudinal flexibility should be such as to enable the catheter to be advanced along the various vascular paths to reach the intended treatment site while retaining the ability to be controllably rotated from its proximal end. The catheter should have sufficient torsional stiffness so that the rotation applied by the physician to the proximal end of the catheter will be transmitted controllably to the distal end.

Figure 3:
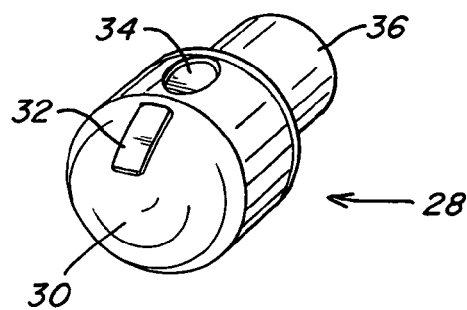
FIG. 3 is an illustration of the distal tip of a monopolar version of the catheter.
Figure 4:
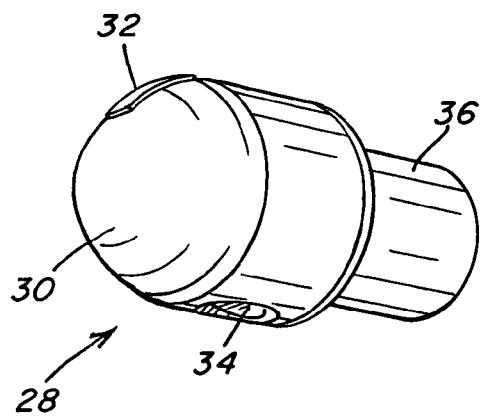
FIG. 4 is illustrates the distal tip of another embodiment of the catheter in which the ultrasonic transducer and RF ablation antenna are disposed on opposite sides of the tip.

FIG. 3 illustrates one embodiment of a distal tip 28 mounted at the distal end 14 of the catheter 10. The tip 28 may be fabricated from a suitable thermoset material having high temperature capability sufficient to withstand temperatures that may be developed by the RF ablation sparking. Materials such as a castable epoxy resin, or a castable ceramic may be used. Alternately, the body of the tip may be machined from a suitable ceramic such as alumina zirconia. The tip 28 may be formed to define a distally-facing leading surface 30 to facilitate its advancement through the patient's vasculature. The tip may have a diameter or cross-sectional dimension of the order of about 1.5 mm. In the embodiment shown in FIG. 3, the tip 28 is monopolar and includes an RF ablation electrode 32 and an ultrasonic transducer 34. In this embodiment, the ablation electrode 32 is disposed distally of the ultrasound transducer 34 and both are angularly aligned with each other along the longitudinal axis of the tip. The ablation electrode 32 and ultrasound transducer 34 may be disposed in other relative arrangements, for example, as illustrated in FIG. 4 in which the ablation antenna 32 and ultrasound transducer 34 are disposed on opposite sides of the distal tip 28. By way of example, one embodiment of the tip may have a diameter about 1.5 mm and a length of about 2.5 mm, not including the proximal stem 36. The electrode may be gold plated, photo-etched stainless steel or machined platinum. These materials provide good electrical conductivity for ablating tissue and are radiopaque to facilitate visualization of the tip under fluoroscopy. The ultrasound transducer may be made from lead zirconate titanate (PZT) or polyvinylidene di-floride (PVDF). The transducer may be between 250 and 650 micrometers in diameter.

Figure 5:
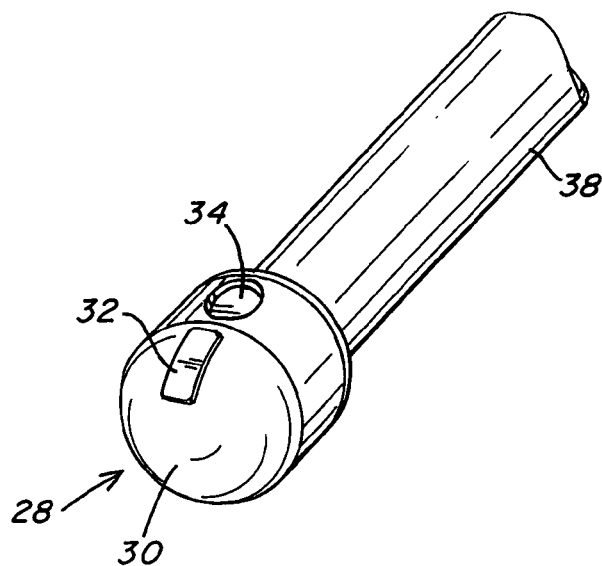
FIG. 5 illustrates one embodiment of a distal tip attached to a catheter shaft coil having torsional stiffness but low flexural stiffness.

The distal tip 28 is attached to the distal end of an elongate shaft indicated generally at 38 in FIG. 5. The shaft is constructed to have sufficient torsional stiffness and longitudinal flexibility so that it can be flexed along curved vascular passages without adversely affecting the ability of the physician to control the angular position of the distal tip 28 by rotating the proximal end of the shaft 38. The shaft should provide the requisite balance of torsional stiffness and longitudinal flexibility. For example, the shaft 38 may be in the form of a coil embedded in a polymer resin that will maintain the coiled diameter while enabling longitudinal flexibility. The distal tip 28 may be formed to include a proximal stem 36 to facilitate attachment of the tip to the distal end of the shaft 38. The stem 36 preferably is dimensioned to fit within the distal end of the shaft and may be secured to the shaft by adhesive or other suitable means.

The invention may be practiced with wire-guided or sheath guided catheters. The sheath guided catheter, for example, may include a tip such as that illustrated in FIG. 3, in which the tip does not include a guidewire lumen. With such catheters, a sheath may be advanced to place the distal end of the sheath adjacent the site of the occlusion so that the sheath can serve to guide the catheter to that site. Placement of such a sheath is well-known and may, for example, by accomplished by the Seldinger technique in which a guidewire is preliminarily advanced to the intended site, the sheath is advanced over the guidewire, and then the guidewire is removed. The proximal end of the sheath may be provided with a fitting adapted to provide a vent at the proximal end of the sheath through which debris or gases generated at the treatment site may be removed. The blood 'pressure within the artery' will tend to cause flow out of the proximal end of the sheath and that rate of flow through the vent can be adjusted, as by an adjustable valve, to a satisfactory rate. In some instances, it may be desirable to apply some aspiration to the sheath, as by connecting an evacuated syringe to a fitting at the proximal end of the sheath. The placement of a wire-guided catheter involves advancement of a guidewire to the treatment site and then advancing the catheter over the guidewire until the distal end of the catheter reaches the treatment site.

Figure 6A:
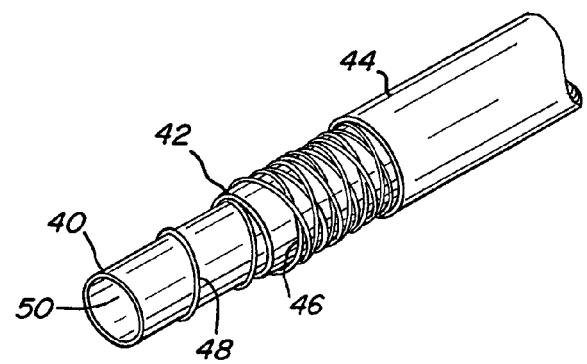
FIG. 6A is an illustration of another embodiment of a catheter shaft.

FIG. 6A illustrates a broken-away segment of a preferred embodiment of a catheter shaft suited for use in the practice of the invention. The shaft may be used with sheath-guided or wire-guided applications and may be formed from three polymeric layers including an inner layer 40, an intermediate layer 42 and an outer layer 44. The layers 40, 42, 44 may be made of a polymer such as Pebax or polyurethane. A tubular mesh of braided stainless steel wires 46 may be disposed between the middle and outer layers 42, 44. For example, stainless steel wire 0.002 inch diameter or 0.001 by 0.003 inch flat wire may be used. The mesh wires 46 can also serve as independent electrical conductors provided that they are insulated from each other. Alternatively, they can serve as a ground wire or an electric shield for the catheter in addition to providing torsional stiffness. Additionally, electrical conductors 48 coiled to minimize longitudinal stiffness, can be disposed between the inner and middle layers 40, 42 of the shaft. The conductor for the RF electrode may be a fine gauge copper magnet wire with a high dielectric coating such as a polyimide or the like. The conductor for the ultrasound catheter may be a micro-coaxial cable. The RF electrode and ultrasound conductor may be twisted in a helical fashion with their associated ground wires to reduce RF interference. The outer diameter of the shaft may be between 3.5 to 4.0 F and the inner diameter of the lumen extending through the shaft may be between about 0.016 to about 0.020 inch. The shaft layers may be fused together to integrate the mesh and conductor wires with the tubular polymeric body. The center lumen 50 of the catheter shaft serves as a guidewire lumen in a wire-guided catheter as well as a conduit for removal of gases and debris that may form as byproducts of the RF ablation process. The length of the catheter may be of the order of 140 centimeters when used in coronary applications although other lengths may be employed, depending on the particular blood vessel and the nature and location of the obstructions involved.

For a wire-guided device the proximal end of the shaft preferably is provided with a Y-body adapter 11 (see FIG. 8), appropriately secured to the proximal end of the shaft by a variety of techniques familiar to those of skill in the art. The axial port for the Y-body may serve as an entrance for a guidewire having a diameter of the order of 0.014 inch. The off-axis arm of the Y-body provides a strain relief for the cable containing the leads to the RF electrode and ultrasound transducer. The length of the cable from the Y-body 11 to the electronic module 18 may be three to six feet with a suitable electrical connector at its proximal end.

Figure 6B:
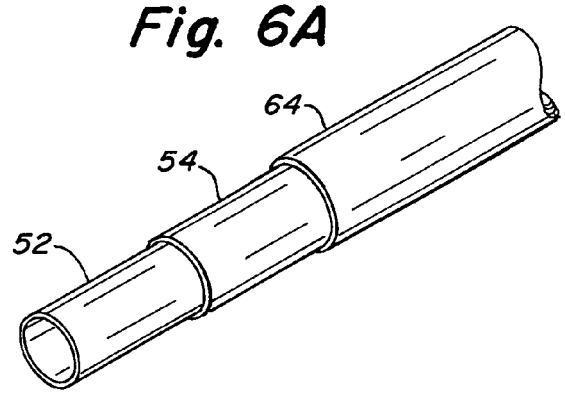
FIGS. 6B-6D illustrate other embodiments of a catheter shaft in which the shaft includes a hypotube construction.
Figure 6C:
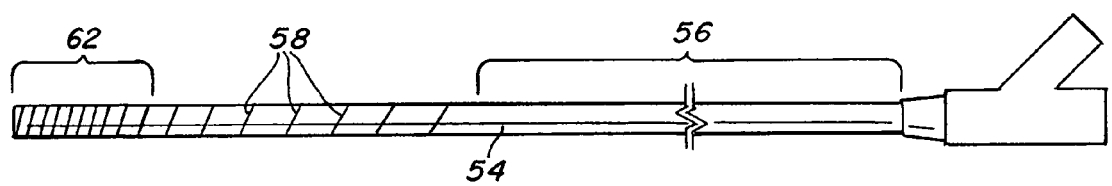
Figure 6D:
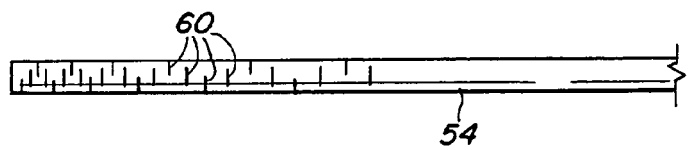

FIGS. 6B-6D illustrate another configuration for the catheter shaft adapted to provide a high degree of torsional stiffness and column strength to resist longitudinal compressive loads on the catheter. In this construction, the shaft includes an inner guidewire tube 52, such as a polyimide tube lined with a low friction material such as PD-Slick tubing commercially available from Phelps Dodge, or a high density polyethylene extrusion. The inner guidewire tube is contained within a hypotube 54 that may be formed from stainless steel or a nickel-titanium alloy or other materials having similar characteristics of torsional and column strength. The shaft preferably is constructed to have increasing flexibility toward the distal regions of the shaft. For example, in the case of a catheter adapted for use with obstructions in a coronary artery, the proximal section 56 including a majority of the length from the proximal end may be formed from the full, uninterrupted, wall thickness of the hypotube 54 (FIG. 6C). In the case of a system adapted to be used with the coronary arteries, the proximal section 56 of the hypotube may be of the order of about 100 centimeters long so that it will remain in the guide catheter and will not enter the curved portion of the aortic arch. The portion of the shaft distal of the proximal section may be made to have increasing flexibility, as by laser machining the hypotube to form selective cuts in the wall of the hypotube. Various patterns may be laser machined in the hypotube such as a helical cut 58 that transforms the tube into a coil configuration. The pitch of the helix can be adjusted to vary the flexibility along the length of the shaft. Alternately, transverse slits 60 or spaces can be formed in a shape and pattern to create miniature hinge points located at circumferentially and longitudinally spaced locations along the shaft (FIG. 6D). Varying the location, size and the distance between the hinge points provides control over the flexibility. Typically, the catheter shaft will be formed so that its most distal section 62, 10-15 cm. in length, will be sufficiently flexible to enable it to traverse coronary arteries. The wiring (not shown) for the ultrasound and RF energy may be helically wrapped about the hypotube and an outer jacket 64 of extruded tubing or heat shrink tubing may be provided as an outermost layer.

Other shaft construction techniques familiar to those in the art may be employed. For example, another type of shaft construction may include a braided stainless steel tube embedded in a selected polymer, such as Pebax, nylon or the like. The relative stiffness and flexibility of various portions of the shaft should be selected to be suited to the particular application. For use in a coronary application, the shaft should have a stiff proximal section, a moderately stiff intermediate section to traverse the aortic arch and a more flexible distal segment adapted to traverse the coronary arteries. Electrical conductors may be embedded in the wall of the braided shaft. The conductors may be embedded using a technique in which the polymer is solution cast over a mandrel, the conductors are spirally wrapped about the initial layer of polymer and an outer layer of polymer is added by dipping or spraying.

Figure 7:
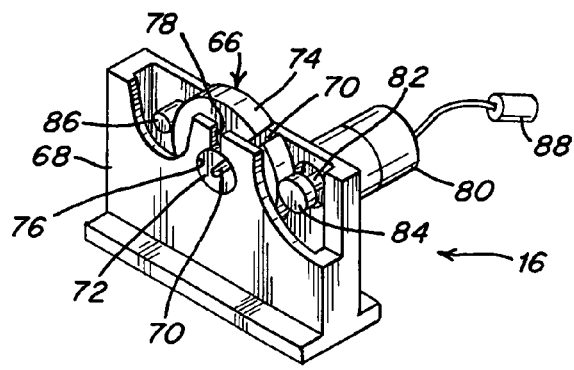
FIG. 7 is a diagrammatic illustration of one embodiment of an angle encoder that is detachably connectable to the proximal portion of the catheter.

FIG. 7 is a diagrammatic illustration of one embodiment of an angle encoder assembly as may be used in the practice of the invention. The angle encoder 16 may include an encoder wheel 66 rotatably mounted in a frame 68 to which other components of the encoder assembly also may be mounted. The encoder wheel may be formed to include a radial slot 70 that extends from the periphery of the wheel 66 to the central axis of the hub 72 of the wheel 66. The encoder wheel 66 may be constructed to have a peripheral surface 74 having a high coefficient of friction so that it can transmit its rotation to a driven wheel of the assembly without slipping. For example, the wheel may be a plastic molded part with an over molded high friction outer ring of silicone or thermoplastic elastomer. The frame is configured to include bearing surfaces 76 to rotatably receive axial extensions of the hub 72. The frame also is slotted, as indicated at 78 along a radial plane that intersects the axis of rotation of the wheel 66 to enable the slot 70 in the wheel to be registered with the slot 78 in the frame so as to permit the catheter shaft 38 to be inserted transversely through the slot 70 into coaxial registration with the wheel 66 and hub 72.

The region of the wheel 66 and hub 72 along the axis of rotation is configured to effect a connection to the catheter shaft 38 so that the shaft and wheel will rotate as one. For example, the innermost extremity of the slot 70 in the hub may be formed to have a non-circular shape, such as square or hexagonal, and a portion of the shaft at the proximal end of the device may be formed with a complementary non-circular shape. The complementary shape may be defined by a molded or otherwise formed sleeve secured to the proximal region of the catheter and provided with the complementary shape. Thus, when that portion of the shaft is inserted fully into the slot 70, the shaft 38 and encoder wheel 66 will be connected to rotate in unison. The connection may be such as to permit relative longitudinal sliding movement of the shaft 38 with respect to the angle encoder 16, if desired. Changes in the catheter angle can be transmitted reliably and accurately to an optical encoding module 80 mounted to the frame. The encoding module 80 includes a shaft 82 having a driven wheel 84 that, in turn, is in non-slipping engagement with the periphery 74 of the encoder wheel 66. This embodiment also includes idler wheels 86 as required to hold the encoder wheel 66 in place and in secure rotation-transmitting engagement with the driven wheel of the encoding module 80. The encoding module 80 includes electrical connectors 88 to transmit power to the encoder module 80 and to transmit signals corresponding to incremental angle changes to the electronics module 18.

Although the angle encoder may take any number of forms, including mechanical and electrical sensors or devices, the preferred embodiment includes an encoding module having a multi-vaned element mounted to the rotatable shaft 82 of the encoder 80. The vanes are arranged so that when rotated they will interrupt an optical beam within the encoding module 80 to create an optically detectable number of pulses from which the extent of angular rotation of the shaft 56 may be determined. The respective radii of the drive train between the encoder wheel 66 and the encoding module determines the degree of resolution of measurement. The multi-vaned element may be formed from a disc of optically opaque material in which a plurality of light-transparent radial slots is formed or a transparent disc with alternating opaque segments.

Figure 8:
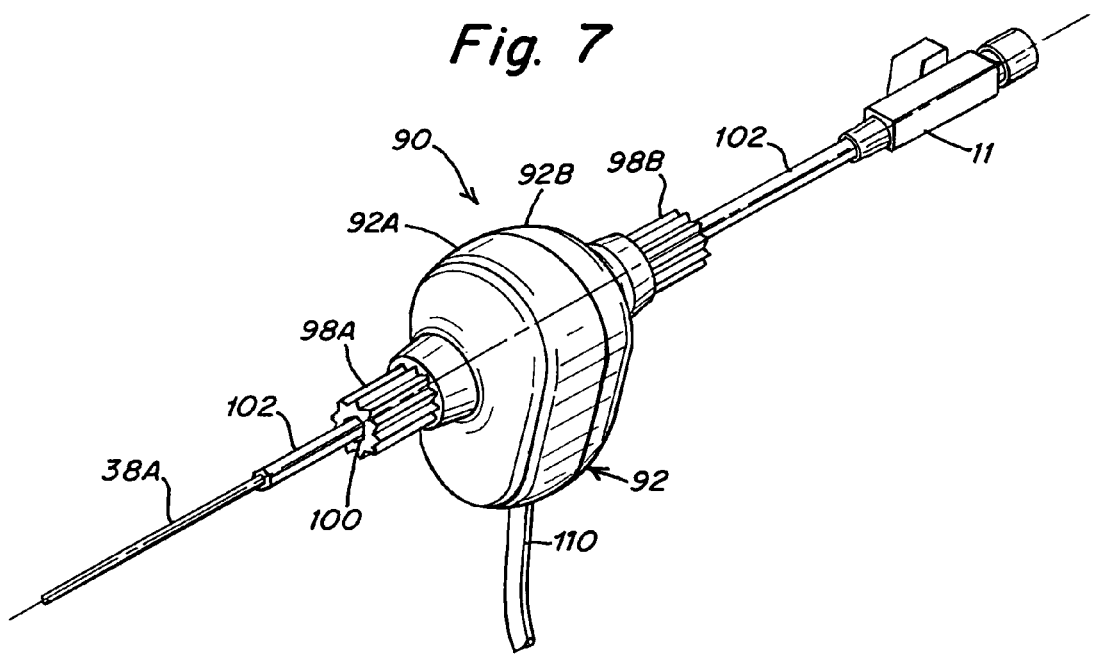
FIG. 8 is an illustration of another embodiment of an angular encoder mounted on the proximal end of a catheter.
Figure 9:
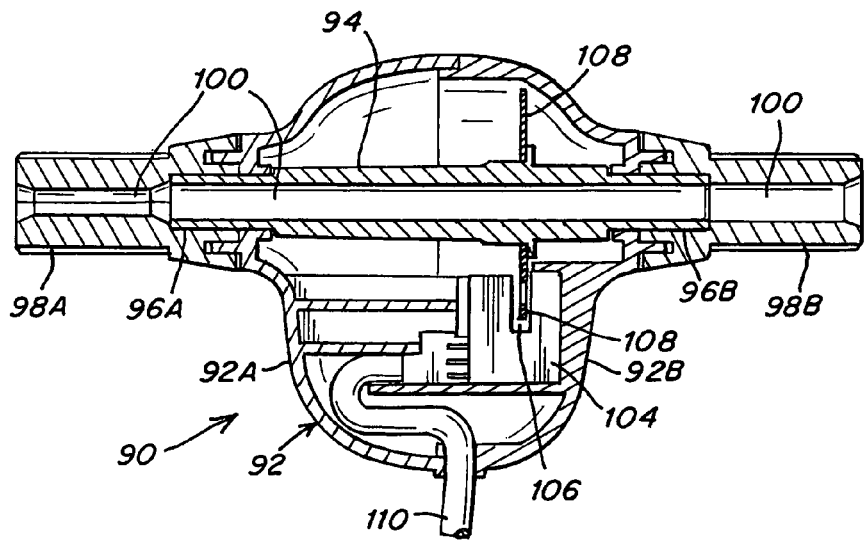
FIG. 9 is a longitudinal sectional illustration of the encoder shown in FIG. 8 with the catheter removed for clarity.

FIGS. 8 and 9 illustrate another embodiment of an angular encoder and mateable catheter. In this embodiment, the encoder 90 includes a housing that may be defined by sections 92A, 92B. A shaft carrier tube 94 is rotatably supported by the housing 92 and has ends 96A, 96B that protrude outwardly from the housing 92. The protruding ends 96A, 96B are secured to knobs 98A, 98B having irregular outer surfaces, such as the fluted surfaces shown in FIG. 8, to facilitate rotation of the shaft carrier tube 94 by rotating either of the knobs 98A, 98B. The device is dimensioned so that the housing 92 can be comfortably held within either of the operator's hands while the thumb and forefinger may be used to rotate one of the knobs. Each of the knobs 98A, 98B and the carrier tube 94 includes a central lumen 100 through which the catheter shaft 38A can be received.

Means are provided to secure the catheter shaft 38A to the rotatable assembly of the carrier tube and knobs 98. One such arrangement is illustrated in FIGS. 8 and 9 from which it may be seen that the portion of the lumen 100 disposed in at least one of the knobs 98A is non-circular in cross-section and is adapted to mate with a complementary non-circular section of the shaft 34. As shown, the lumen 100 in the knob 98A may be hexagonal and adapted to mate with a hexagonal section on the catheter shaft 38. The hexagonal section on the shaft may comprise an extruded polymeric tube having an inner surface adapted to closely fit and be secured, as by adhesive, to the outer surface of the guidewire. The extrusion 102 is formed with an outer hexagonal surface to mate with the corresponding surface in the central lumen. The tolerances between the outer hexagonal surface of the extrusion and the inner hexagonal surface defined through the lumen 100 may be such as to permit relative longitudinal sliding movement of the encoder 90 relative to the catheter but to provide a sufficiently secure connection to enable transmission of rotational information from the encoder. The extrusion 102 may be of the order of 10-15 cm. long and may be secured at the proximal end of the catheter shaft. In the embodiment illustrated in FIGS. 8 and 9 the encoder 90 and catheter are assembled by backloading the encoder onto the distal end of the catheter and sliding it toward the proximal end into mating engagement with the complementary portion of the extrusion 102. Although the preferred embodiment provides, for detachable connection between the encoder and the catheter, other non-detachable arrangements may be provided to secure the catheter shaft and rotatable assembly so that they will rotate in unison, such as direct bonding, clamping arrangements or the like.

In the preferred optical encoder embodiment, the housing contains an LED photodiode assembly 104 with light emitting diode and photodiode components being disposed on opposite sides of a transverse slot 106 formed through the assembly 104. The LED and photodiodes are optically aligned. A light beam interrupter in form of a vaned interrupter disc 108 is mounted to the shaft carrier tube 94 so that it will rotate in unison with the tube 94 and the catheter shaft 38A that extends through the encoder 90. As the operator rotates one of the knurled knobs, the catheter and the interrupter disc 108 rotate in unison so that the vanes of the disc alternate between breaking the path of the light and passing the light to the photodiodes. A cable 110 transmits the signals from the photodiodes to the electronics module 18 where the rotation angle of the catheter can be determined precisely and the ultrasonic echoes that are received from the transducer at the tip of the catheter can be placed in their correct angular orientation. The cable also may carry power necessary to illuminate the LED.

The photodiodes may be used in a quadrature configuration to sense the angle and direction of rotation. This technique, familiar to one skilled in the art, entails receiving the light from the LED using two photodiodes (photodiode "I" and photodiode "Q") spaced slightly apart from one another so that if the vanes are spinning in a counterclockwise direction the signal generated in photodiode "I" has a phase lead with respect to photodiode "Q" and if the vanes are spinning in the clockwise direction, the signal on photodiode "I" has a phase lag with respect to photodiode "Q". In some instances, it may be desirable to initiate operation of the ultrasound system only in response to rotation of the catheter in one direction. To that end, the circuitry and software by which the system is controlled may include a control by which the triggering of the ultrasound in response to rotation of the catheter is disabled when the catheter is rotated in a selected direction. Thus, the system may be set up so that rotation of the catheter in either direction will initiate the ultrasound functions or it can be set up so that the ultrasound system will be initiated only when the catheter is rotated in one, operator-selected direction.

Among the advantages of the invention is that it enables the use of a catheters and angle encoding devices that can be fabricated at very low cost and, therefore, that lend themselves to one-time disposable use.

Figure 10:
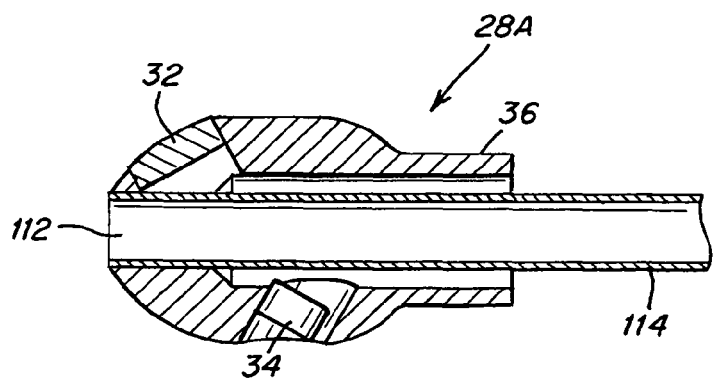
FIG. 10 is a sectional illustration of an embodiment of the distal tip of the catheter of the type shown in FIG. 3 that includes a lumen through which a guidewire may be received and through which debris and gases from the RF ablation process may be removed.

FIG. 10 illustrates another embodiment of a tip 28A that includes a central guide wire lumen 112. The guidewire lumen 112 may be defined by a tube 114 that is attached, as by adhesive, to the distal tip 28A and extends through the catheter shaft to the Y-body (see FIG. 8) at the proximal end of the shaft. The tube 114 may have an inner diameter large enough to enable a guidewire of the order of 0.014 inch diameter to pass through the lumen 112. The lumen 112 also provides a path through which debris and gases caused by the RF ablation process may be removed.

The catheter shaft 38 carries conductors by which the electrical signals from the RF ablation antenna 32 and the transducer 34 are transmitted between the distal tip and the electronics module 18. In a monopolar device, two conductors are employed, one serving as a ground or reference wire and another to carry an ultrasonic transmit pulse to the ultrasonic transducer 34 and to carry the echo signals returned from the tissue back to the electronics module. A third conductor carries the RF ablation energy to the RF antenna 32. The antenna 32 should be surrounded by an insulative material that may comprise the material from which the tip is formed.

Figure 11A:
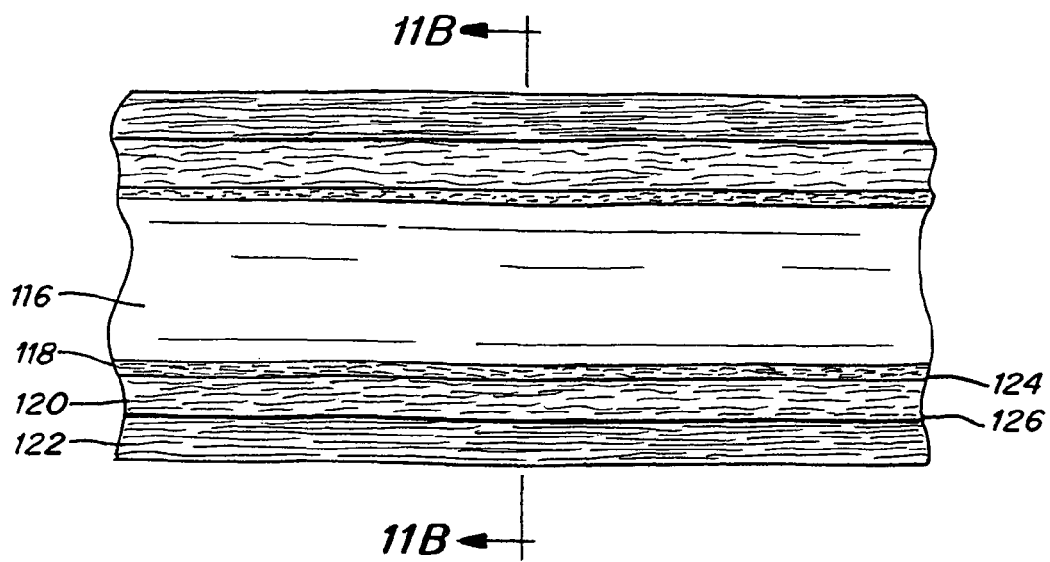
FIG. 11A is a diagrammatic longitudinal sectional illustration of a portion of an unobstructed, native artery illustrating its layers.
Figure 11B:
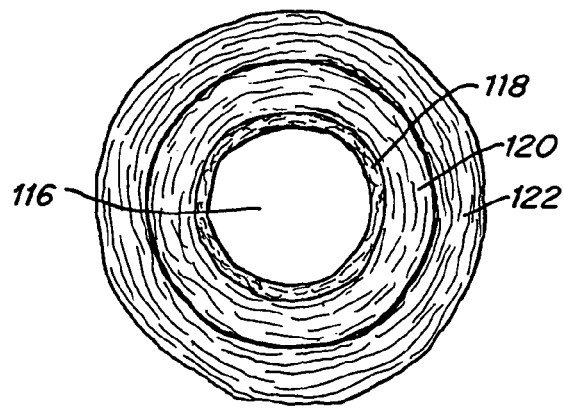
FIG. 11B is a transverse sectional illustration of an artery as seen along the lines 11B-11B of FIG. 11A.

FIGS. 11A and 11B illustrate, diagrammatically, the layers of a normal artery. The innermost layer that defines the lumen 116 of the artery comprises the intima 118. In a healthy artery, the intima is relatively thin. As plaque develops and infiltrates the intima, it increases in thickness. A middle layer, that includes the medial layers 120, surround the intima, includes smooth muscle tissue and provides structural integrity for the artery. The outermost layer is the adventitia 122, typically comprising fibrous tissue such as collagen. The media is made up of three layers that include two thin elastic layers, an inner elastic lamina 124 and an outer elastic membrane 126 along with the thicker muscular media.

Figure 12A:
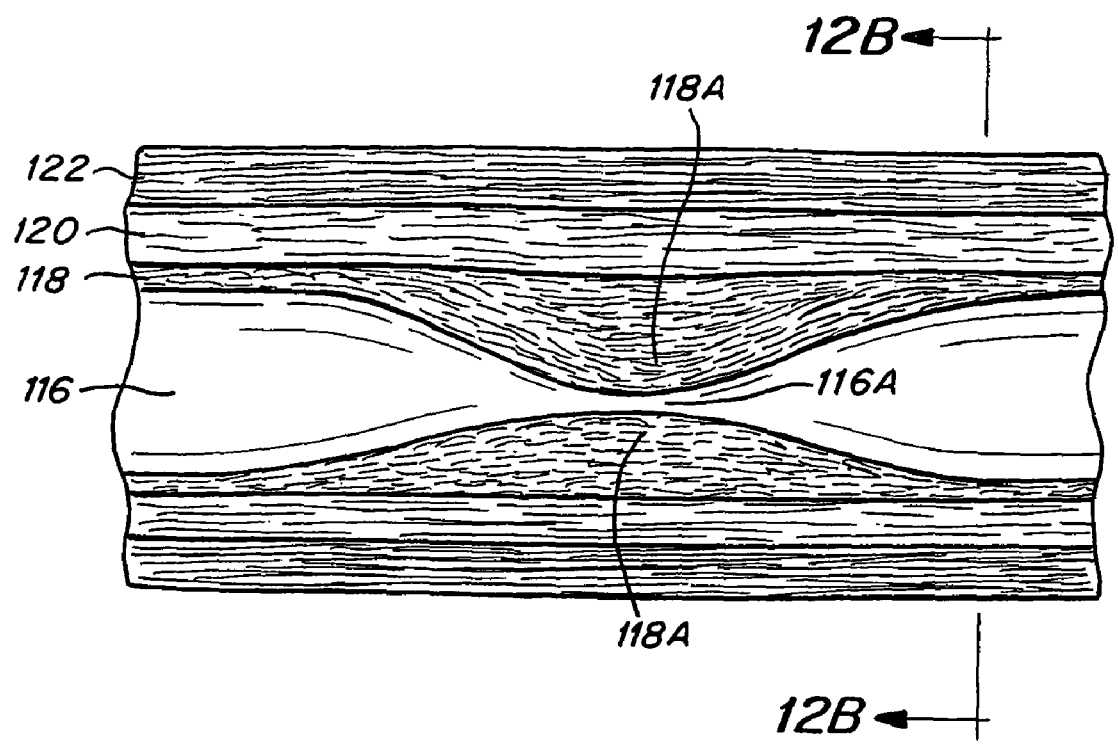
FIG. 12A is a diagrammatic illustration similar to that of FIG. 11A but in which the artery is nearly totally occluded.
Figure 12B:
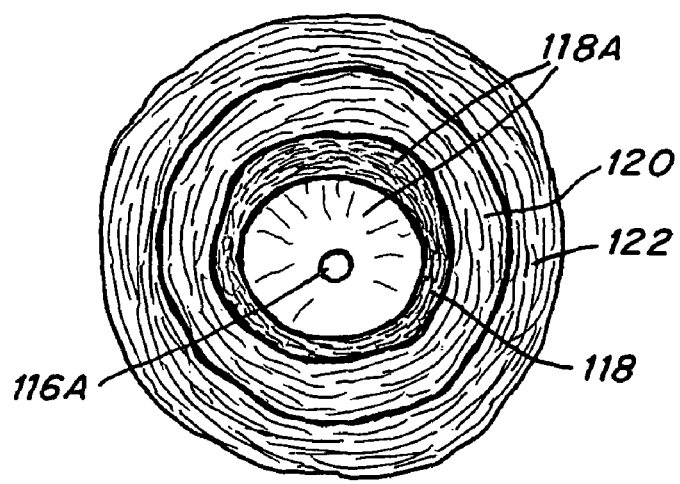
FIG. 12B is a transverse illustration as seen along the line 12B-12B of FIG. 12A.

FIGS. 12A and 12B illustrate, diagrammatically, an artery in which the lumen 116 has been compromised by atherosclerosis. The obstruction is depicted as being caused by an increased thickening in the intima 118, as indicated at 118A. Intima thickening develops from deposition of atherosclerotic plaque within the intimal layer. Thrombus also may build up on the luminal surface of the intima (not shown in FIGS. 12A and 12B). When the arterial lumen 116 is severely obstructed, such as indicated at 116A, or is totally occluded, the physician may not be able to advance a catheter or a guidewire through the stenosis. The present invention provides means by which a passage may be formed through the artery of sufficient dimensions to enable a guidewire and therapeutic catheters to be placed within the stenosis to further enlarge the cross-section of the lumen to enable or enhance blood flow.

In order to reduce the risk of perforating the blood vessel by the application of RF energy, it is important for the physician to be able to visualize the structure of the artery sufficiently to assess and distinguish those regions that are more susceptible to perforation. Of particular interest in arteries are the boundary regions that define the medial structure including the media 120 and the internal elastic lamina and the external elastic membranes 124, 126. It should be understood that in the use of intravascular ultrasound imaging systems, the image may not provide a precise indication of the location of the inner elastic lumina and the innermost boundary of the media. This may occur as a result of intrusion of plaque into the region of the internal elastic membrane so that it is difficult to obtain a clear boundary surface capable of reflecting ultrasound waves. The outer boundary of the media, along the interface with the external elastic membrane may provide a more definable ultrasound image and, therefore, the physician may use the ultrasound to identify and locate any of the structures that comprise the medial layers as a reference for the location of the boundary of the native artery.

In the illustrative embodiments the ultrasound transducer is oriented at an angle to the longitudinal axis of the device so that as the transducer is rotated, it will emit ultrasound in a somewhat conical, forwardly oriented pattern. The resulting image thus is not a purely planar cross-section but, instead, is a conical, forward looking image. The viewable image may be modified to convey to the observer a sense that the image is conical and not that of a transverse plane. For example, the image may be in the form of a false color display in which coloring characteristics can be varied (e.g., hue, saturation, intensity) to indicate visual differences as a function of the radius from the center of the image. In this instance, the forward distance, along the longitudinal axis of the catheter, of a particular point on the cone being imaged will be a direct function of the radius on the display. Thus, the image of points lying at a specific radius from the center of the image can be displayed to be visually distinguishable from those at a different radius and, therefore, at a different axial location.

Once the physician has approximated the media, the catheter is positioned so that its RF ablation antenna faces away from the closest region of the medial layers. That location is determined by the operator rotating the catheter to generate an image of the vessel on the display monitor. When the closest part of the media is located, the RF ablation antenna is oriented to face away from that location, the objective being to assure that RF ablation energy is not applied in a location that might have an increased risk of perforation of the medial layers. With the RF ablation antenna so located, the RF ablation circuit is then activated manually by the physician, as by stepping on a foot switch, to ablate a small amount of tissue.

The catheter then is advanced into the ablated void. Since the electrode is located on one side of the distal tip, the void will be on that side of the tip so that advancing the catheter causes the tip region to curve toward and into the void, thereby steering further away from the previously imaged medial layers. The physician again rotates the catheter to trigger the ultrasound system and obtain another image to determine the closest position of the medial layer. The RF ablation antenna is again oriented away from the closest medial location and the RF ablation circuit is again activated. The procedure is repeated until the occlusion has been crossed. Once the occlusion has been crossed the ablation catheter can be removed and a guidewire can be advanced through the region of the stenosis. With the guidewire so placed, other therapeutic catheters such as balloons, stent deployment catheters, other plaque removal devices and the like can be advanced over the guidewire to complete the therapeutic treatment.

FIGS. 4 and 10 illustrate a modified embodiment of the catheter distal tip in which the RF ablation antenna 32 and ultrasonic transducer 34 are angularly displaced about the tip axis and may be on opposite sides of the tip. With this embodiment, when the operator has rotated the catheter to direct the transducer toward the portion of the vessel closest to the medial layers, the RF ablation antenna will already be positioned oppositely and in readiness for activation. In some instances, the thickest portion of the plaque or plaque-laden intima may be located diametrically opposite the least thickened intima region or close to a diametrically opposite location. In those instances, employing a tip in which the ablation electrode is disposed opposite from the ultrasound transducer may make it easier for the physician to rotate the catheter to an orientation in which it is safe to ablate.

Figure 13:
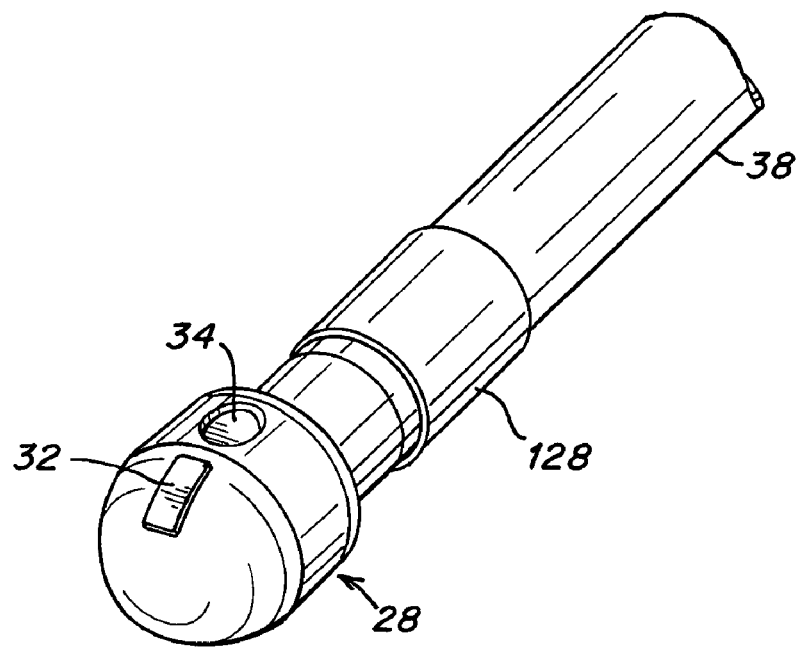
FIG. 13 is an illustration of the distal tip of a bipolar embodiment of the catheter.

The above-described devices are monopolar and are used in conjunction with an electrically grounded patient plate. FIG. 13 illustrates a bipolar embodiment that includes a passive ground electrode 128 mounted proximally of the active RF antenna. The ground electrode should have a significantly larger surface area than the active electrode to prevent sparking or heating near the ground electrode. Such an embodiment has the advantage of reducing electrical currents in regions that are more distant from the catheter tip and that might cause muscle twitching and abnormal heart rhythms.

Figure 14:
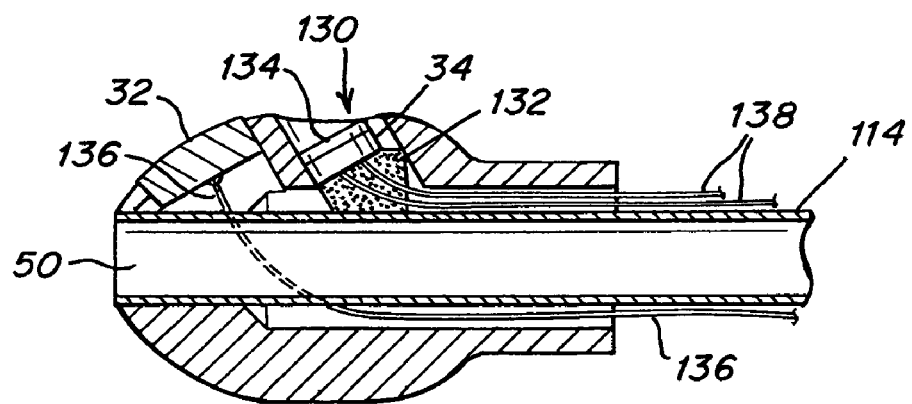
FIG. 14 is a cross-sectional illustration of an embodiment of a tip similar to that of FIG. 5 but with the RF electrode and ultrasound transducer in aligned angular positions and with an absorptive backing and matching layer for the transducer.

FIG. 14 illustrates additional details of a distal tip for an over-the-wire catheter. The tip has a central tube 114 that defines a lumen 50 receptive for a guidewire or for flushing and removal of debris. Although the ablation electrode 32 and transducer assembly 130 are shown as being disposed on the same side of the distal tip, they could be on opposite sides as described in connection with the embodiment of FIG. 4. The ultrasonic transducer assembly 130 includes the ultrasonic transducer 34 and a transducer backing 132 adapted to absorb ultrasonic waves emitted from the backside of the transducer. Such waves otherwise could interfere with the echoes returning to the front face of the transducer, causing artifacts in the image. In order to permit the tip to include both the lumen 50 and a suitable absorptive backing 132, it is preferable to utilize a deformable or shaped backing that is bent along the axis of the catheter tip thereby to provide a longer distance over which the back-directed waves can be attenuated. Such backing materials are well known and can be made from epoxies or other polymers loaded with tungsten, lead or other suitable materials. When the glass transition temperature of the epoxy is exceeded the backing can be deformed into a new shape and when cooled below the glass transition temperature the new shape will be maintained. Alternatively the entire distal tip of the catheter could be molded or machined out of an appropriate transducer backing material. The transducer assembly 132 also preferably includes a matching layer 134 to couple the ultrasound from the high acoustic impedance piezoelectric transducer 134 to the lower acoustic impedance of human body tissue by acting as a quarter wave transformer. FIG. 14 also illustrates the conductor 136 that carries the RF ablation energy from the electronics module 18 to the RF antenna 32. Coaxial conductors 138, in this embodiment, carry ultrasonic signals to and from the ultrasonic transducer.

FIGS. 15A-15D show another embodiment of a catheter having a catheter tip 140 in which the tip has a wide, flat ablation electrode 142 on one side of the distal tip and a contoured surface 144 on the opposite side adapted to engage the ablated cavity to direct the tip into the cavity. By way of dimensional example, the distal tip shown in FIGS. 15A-15D may be approximately 1.5 mm. wide (as viewed in plan in FIG. 15D) and about 3 mm. long. The thickness, between the electrode 142 and the contoured surface 144 may be of the order of 1.1 mm. The guidewire lumen 146 may be of the order of 0.16 inches diameter to receive a guidewire 0.014 inches in diameter. The width of the electrode may be at least half that of the body of the tip.

Figure 15A:
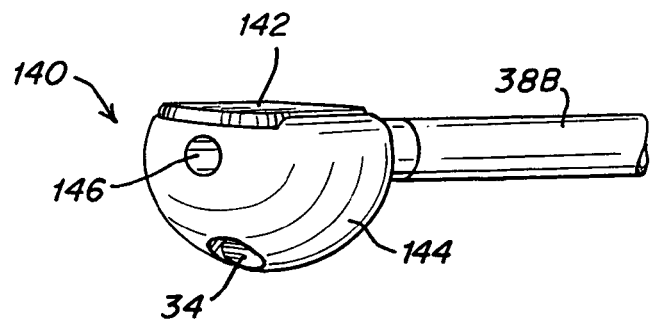
FIGS. 15A-15D illustrates another embodiment of the catheter tip with a broad RF electrode on one surface and a guiding contour on the opposite surface.
Figure 15B:
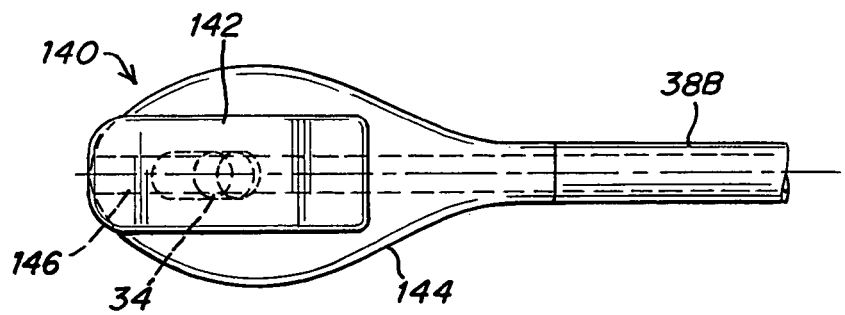
Figure 15C:
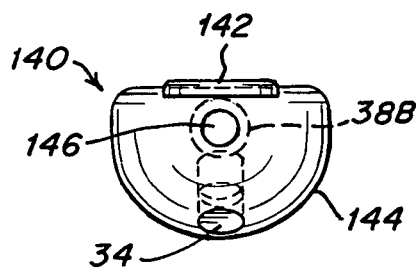
Figure 15D:
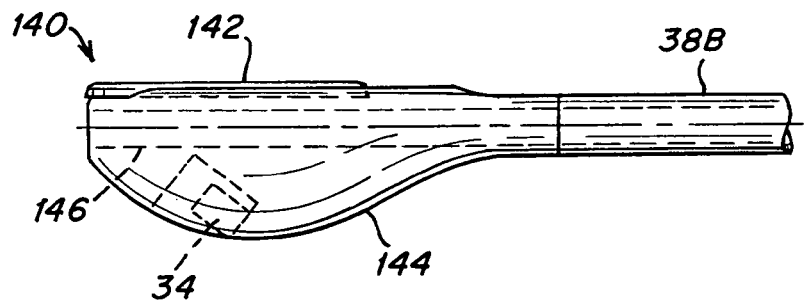
Figure 16A:
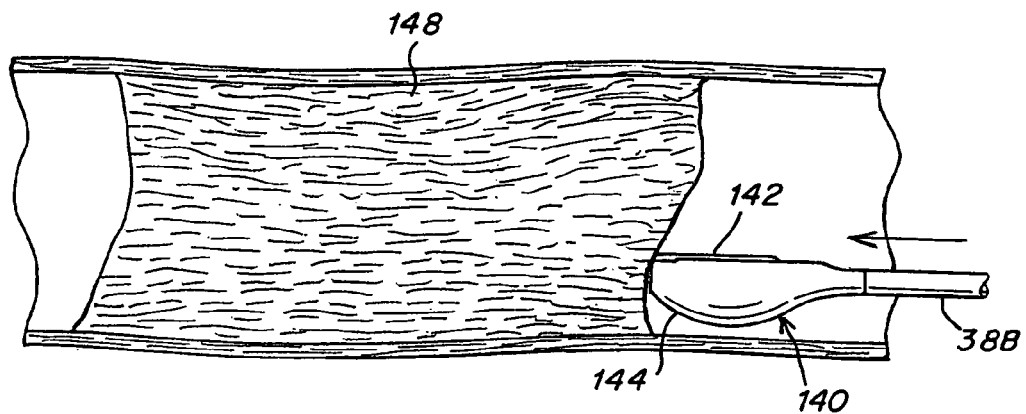
FIGS. 16A-16E are diagrammatic illustrations of the manner in which the catheter having a tip depicted as in FIGS. 15A-15D may advance through a total occlusion.
Figure 16B:
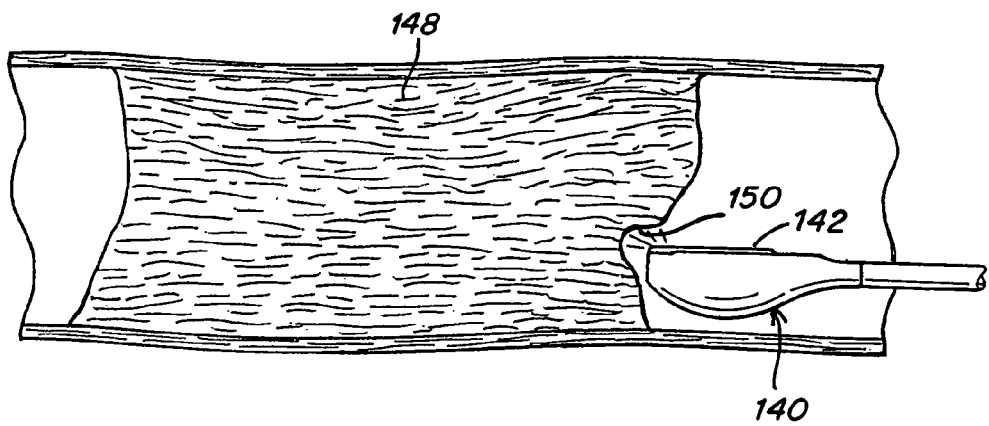
Figure 16C:
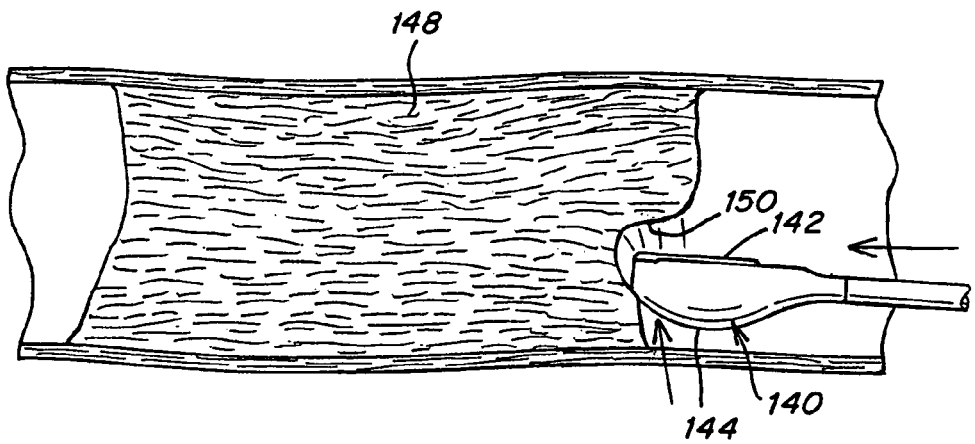
Figure 16D:
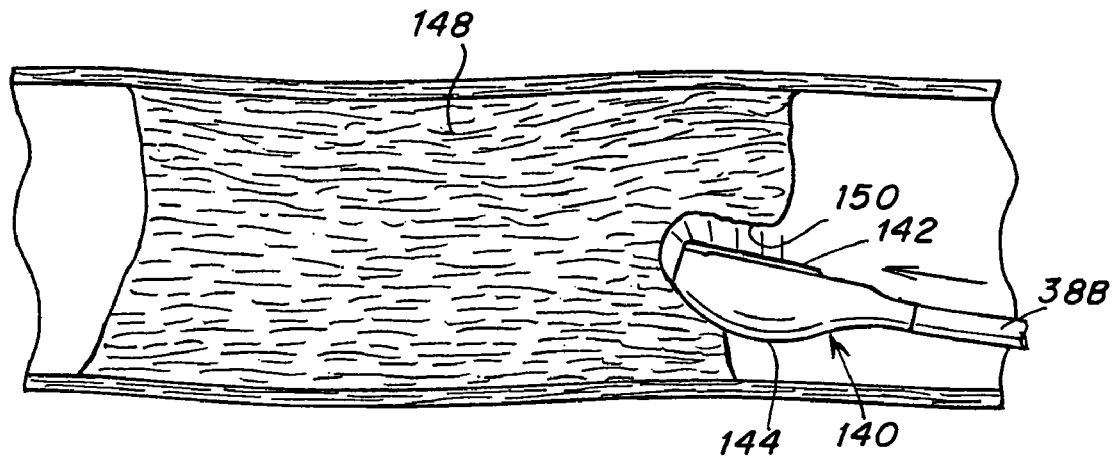
Figure 16E:
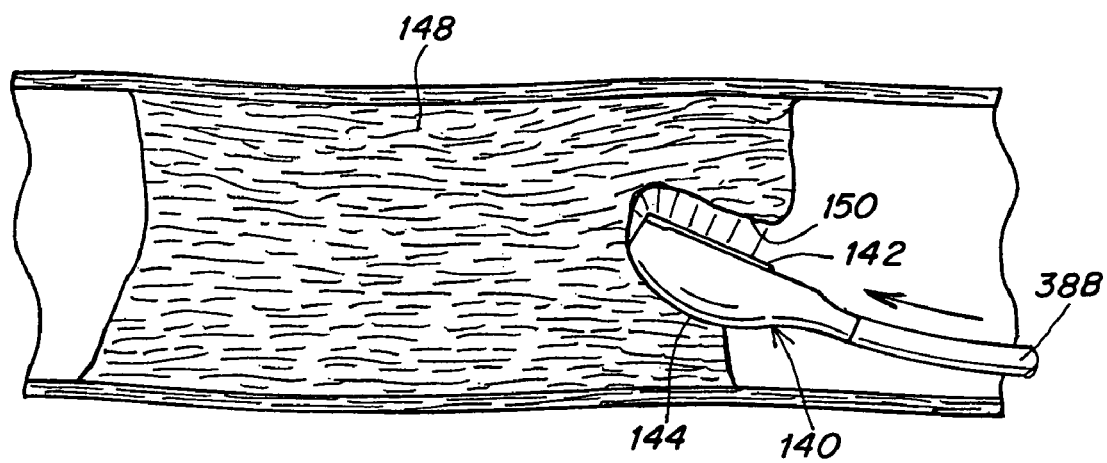

FIGS. 16A-16E illustrate, diagrammatically, the progression of the catheter 38B having a tip as shown in FIGS. 15A-15D through a total occlusion 148. FIG. 16A illustrates, diagrammatically, the catheter tip 140 in engagement with the occlusion 148 and positioned so that the electrode will ablate in a direction away from the closest portion of the medial layers of the artery. When the RF electrode is energized (FIG. 16B), a small cavity 150 is created above and in front of the catheter tip 140. The RF electrode 142 is dimensioned with respect to the amount of energy that will be applied and with respect to the dimensions of the distal tip 140 so that the cavity created by the ablation is large enough to receive the leading end of the catheter tip 140. When the operator pushes the catheter forward (FIG. 16C), the wedge-like contoured surface 144 will cause a bending moment to be exerted on the distal tip, curving the catheter in the direction of the cavity. In order to enter the cavity (FIG. 16D), the catheter must flex to accommodate the contoured surface 144 (FIG. 16E). The region of the shaft just proximal to the tip, being more flexible than more proximal portions of the shaft, should be sufficiently flexible to permit such flexure. As the procedure is repeated, the catheter continues to follow a curved path until the electrode 142 is rotated to another angle about the axis of the device and the process is repeated in a direction consistent with that new angle. In order to facilitate rotation of the catheter tip within the ablated cavity, the contoured surface 144 of the tip opposite that of the RF electrode may be rounded and, as seen in FIG. 15C, the surface may have a smooth, bulbous, arcuate cross-section, such as an approximately semicircular cross-section shown. The guidewire lumen 146 facilitates the placement of a guidewire and the removal of ablation byproducts.

Figure 21:
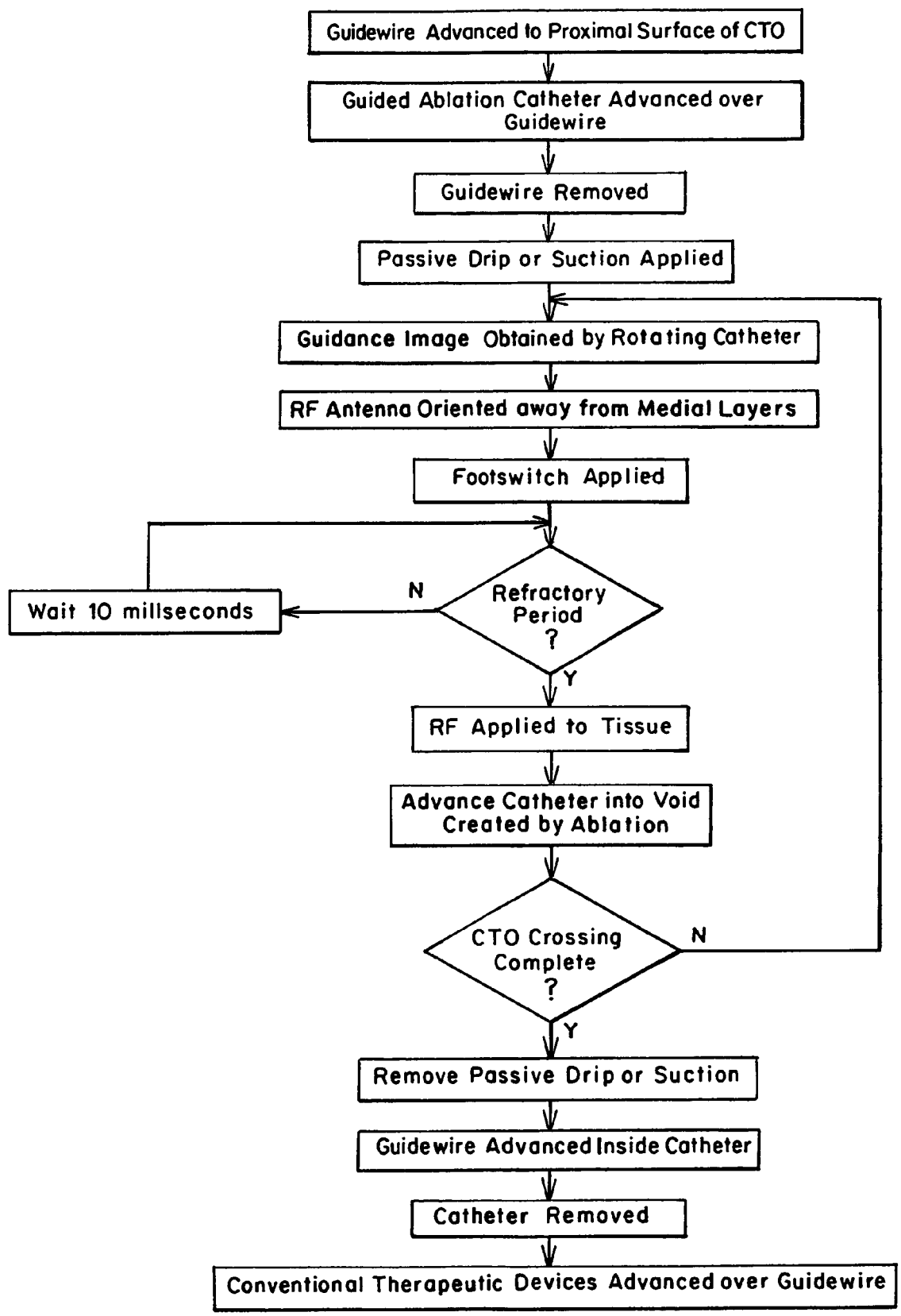
FIG. 21 is a flow diagram illustrating the method of use and operational sequence of the system.

FIG. 21 is a flow diagram of the procedure sequence for a wire-guided catheter in accordance with the invention. Initially, a guidewire is advanced through the patient's vessels to locate the distal end of the guidewire at the proximal surface of the stenosis or total occlusion. A wire-guided ablation catheter then is advanced over the guidewire to position its distal tip at the occlusion. The guidewire then may be removed and passive drip or suction applied at the Y-fitting on the proximal end of the catheter. With the electronics systems on and in operation, the physician manually rotates the catheter either directly or by operation of the angle encoder, causing an ultrasound image to be obtained and displayed on the monitor. Based on the image information, the physician orients the catheter so that the RF electrode is oriented in a direction that will minimize risk of damage to the medial layers of the artery. When the catheter is oriented as desired, the foot switch is triggered and, upon detection by the system that the heart is in its refractory period, an RF signal is applied to the electrode and to the tissue to ablate a portion of the tissue. The catheter then is advanced into the ablated void. If the occlusion has not been completely crossed, the physician will again rotate the catheter to obtain an updated image and will relocate the RF antenna to a desired location. The foot switch then is triggered and the process repeats until the occlusion has been crossed. The passive drip or suction then may be shut off. A guidewire then is advanced through the guidewire lumen of the catheter and through the ablated passage through the occlusion. The catheter then is removed and the guidewire can be used to guide conventional therapeutic devices along the guidewire, to the site of the stenosis where further treatment can continue.

Figure 17A:
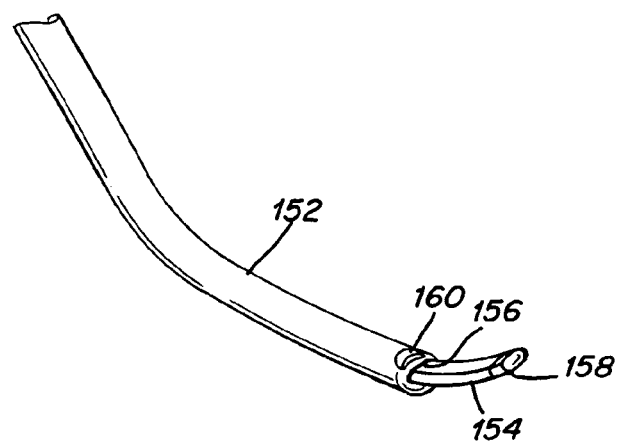
FIG. 17-A illustrates another embodiment of a combined IVUS and RF ablation catheter in which steering is effected by a combination of a keyed guidewire and an RF ablation sheath.
Figure 17B:
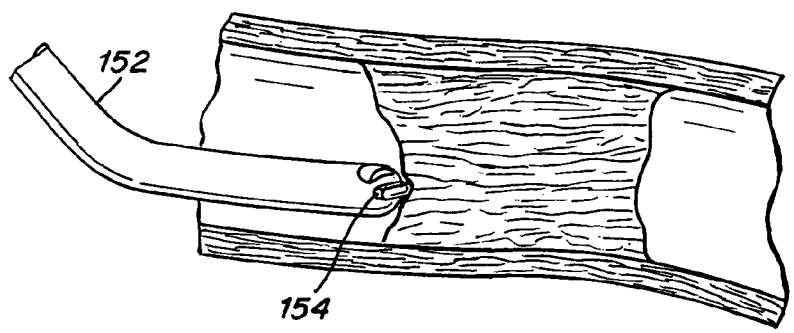
Figure 17C:
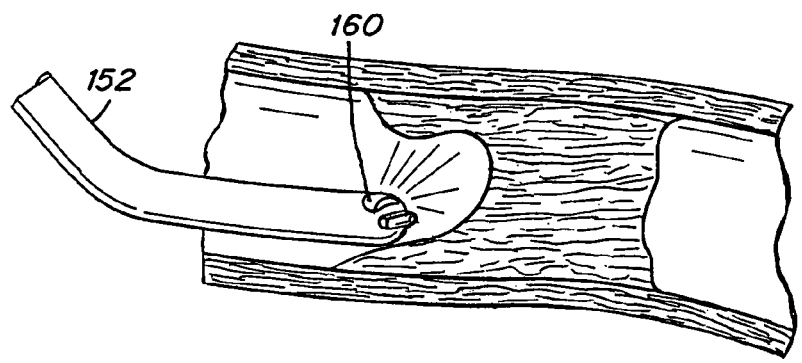
Figure 17D:
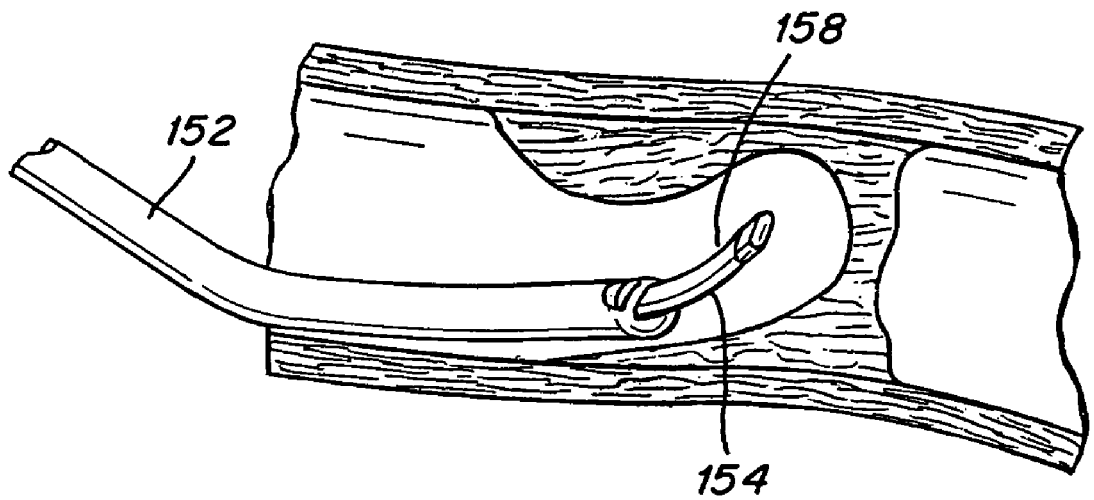
Figure 17E:
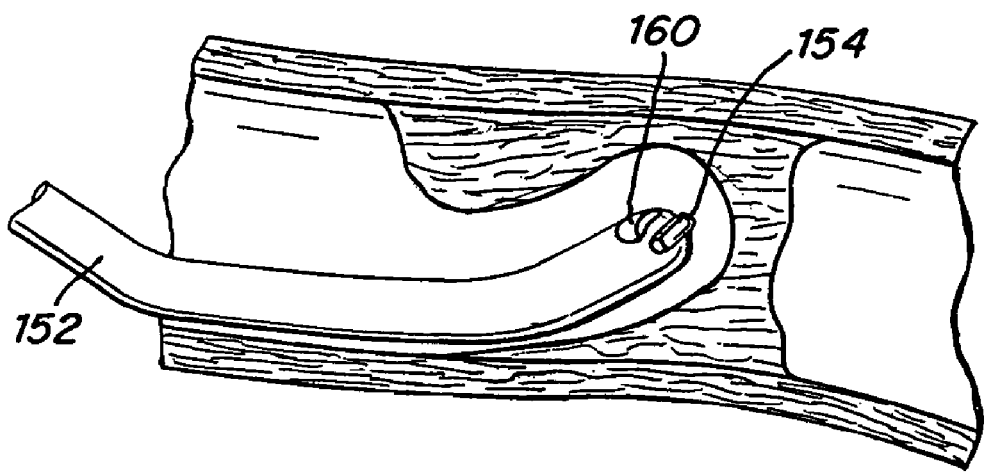

In some instances, as where the severe or total occlusion can be determined to be very short and with low risk of vessel perforation of dissection, it may be possible to omit the ultrasound feature from the catheter. FIG. 17A illustrates one type of intravascular catheter system adapted for spark ablation of such short and low-risk severe stenoses and total occlusions. In this type of catheter, the system includes a catheter body 152 and a guidewire 154, the body 152 including a lumen 156 that receives the guidewire in a keyed, slidable, relationship such that the guidewire 154 cannot be rotated but can slide relative to the catheter body 152. The distal end of the guidewire 154 is formed so that when it is in its relaxed state, as when it is protruding out of the distal end of the catheter, it will assume a predetermined non-linear shape such as a curved shape 158 as suggested in FIG. 17A. The distal tip of the catheter 152 also includes an RF ablation electrode 160. The curved tip 158 of the guidewire is sufficiently flexible so that it can be withdrawn into the lumen 156 of the catheter 152, with the curved tip 158 straightening as it is drawn into the catheter 152 (FIG. 17B). The relative flexibilities of the curved tip of the guidewire and the distal portion of the catheter should be balanced so that when the tip is advanced into a secure position in the ablated void, the catheter can be advanced and guided by the distal end of the guidewire without straightening and pulling the guidewire out of position from within the ablated void. The curved catheter tip 158 is constructed so that in its free, unconstrained state, it will lie in a plane that also includes the RF electrode. Thus, after a cavity is created by the activation of the electrode (FIG. 17C), the cavity can be entered by the tip 158 of the guidewire as the guidewire is advanced from the sheath (FIG. 17D). Once the tip of the guidewire is securely in the cavity, the sheath can then be advanced over the guidewire into the cavity (FIG. 17E). The angle and therefore the direction of the next ablation then can be selected and the process repeated. The keyed relationship of the guidewire and catheter assures that the bend at the distal tip of the guidewire will be in the direction of the most recently formed cavity. It should be understood that although this embodiment, without ultrasound capability, is particularly adaptable to special circumstances where ultrasound imaging may not be necessary, an ultrasound transducer could be mounted to the distal tip of the device, for example, at a location opposite that of the ablation electrode. Such an RF ablation catheter may also be employed with other commercially available, non-keyed formable guidewires. In such a case the physician may use fluoroscopy to assure that the tip of the guidewire enters the ablated cavity.

The guidewire 116 may have a construction as illustrated in FIGS. 18A-18E that includes a core wire 162 formed from stainless steel or a nickel titanium alloy, centerless ground with barrel grinds and tapers along the distal twenty to thirty-five cm. of the core wire to provide the desired degree of flexibility and support along its length. A distal segment of the core, about three to five cm., may be covered with a platinum or other radiopaque coil 164. The distal portion of the core wire preferably should be flattened, as indicated at 166, to a ribbon cross-sectional shape to establish a preferred bending plane for that portion of the guidewire. The proximal portion of the core wire may be provided with a polymer sheath 168 having an outer diameter corresponding to that of the coil. In order to enable the guidewire to be non-rotatably keyed to the catheter, the ribbon portion 166 may be over-molded with a flexible polymer or elastomeric member 169 to have a non-circular cross-section, preferably oval. The bend in the distal tip is formed after the wire is constructed, aided with the use of a bending fixture. By way of example, the oval cross-section of the polymeric member 169 may have a minor diameter of about 0.010" to 0.016", with 0.014" being a preferred dimension. The major diameter may be about 0.025 to about 0.035" with a preferred dimension of about 0.030". The length of the polymeric tip cover may be between about 0.05 to about 3.0 cm., with a length of about 1.5 cm. being preferred.

The tip of the catheter 152, shown diagrammatically in FIGS. 19A-19C, is provided with an inner luminal segment at its distal end having a matching oval cross-section opening and is provided with sufficient clearance (e.g., 0.017"×0.033") to permit easy longitudinal movement of the oval-shaped tip of the guidewire. The catheter lumen proximal of the oval section is round and slightly larger diameter than the major axis of the tip cover (e.g., about 0.034" to about 0.037"). That will allow the keyed guidewire to be removed from the catheter in the event it is desired to exchange it for a standard circular cross-section guidewire after the occlusion has been crossed. In order to maintain the keyed relationship of the guidewire 164 and the catheter 152, a stop preferably is mounted to the proximal end of the guidewire, proximally of the proximal end of the catheter 152. The stop should be located to limit the extent to which the guidewire 164 can be cause to protrude out of the distal end of the oval opening 171. Thus, the oval-shaped cover 169 cannot be projected beyond the keyed opening 171, assuring that the keyed orientation will be maintained.

The catheter 152 may be formed from a stainless steel braided shaft embedded within a Pebax or similar polymer for most of the length of the catheter except for the most distal 10-15 cm., in order to maintain shaft flexibility. The tip preferably is a molded high temperature material (e.g., LCP, Peek) to which the electrode 160 is attached. The catheter 152 preferably has a smaller diameter in its distal region (e.g., 3 to 3.5 French) than in its more proximal regions (e.g., 4.5 French).

Figure 20:
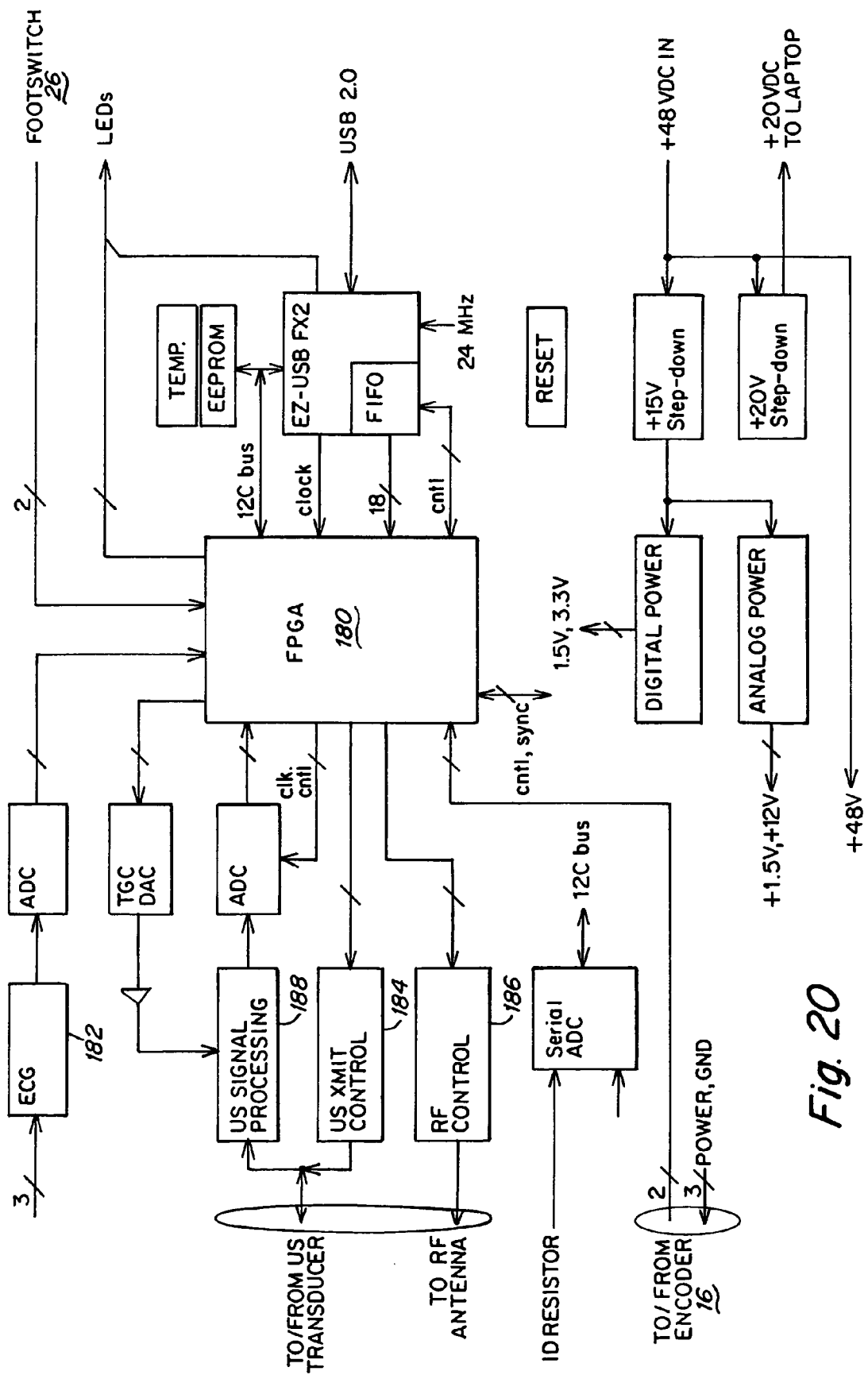
FIG. 20 is a block diagram of the control circuitry of the electronics module.

FIG. 20 is a block diagram of a portion of the electronics module 18 by which the operation of the device is controlled. The module includes a field programmable gate array 180 that is connectable through a USB 2.0 interface to the computer. When the system is turned on, the computer programs the gate array to perform the various control functions for the system. The system then remains in a quiescent state awaiting various inputs by which the operation of the ultrasound and ablation circuits are controlled. Thus, the field programmable gate array receives input from the patient's electrocardiogram 182, from the angle encoder 16 and from the operator-controlled foot switch 26. When a signal is received from the angle encoder indicating that the catheter has begun to rotate, the gate array 180 will signal an ultrasound transmit control 184 that, in turn, energizes the ultrasound transducer to emit ultrasound signals and receive the echoes. In this embodiment the echoes are conducted from the transducer and are processed through an analog pre-amplifier, a time gain control stage and a logarithmic detection circuit 188. Once digitized, the signals are sent, through the gate array 180 for digital signal, processing and then to the computer where imaging software further processes and presents an image of the artery on the monitor 21. The image remains in place for a predetermined time after the rotation of the catheter has stopped. Should the operator determine that the ablation electrode is in a desired orientation and location to initiate ablation, the foot switch 26 is activated. The gate array 180 delays the RF switch signal until it has determined that the patient's ECG 182 indicates that the patient's heart is in its refractory period, at which time the gate array triggers the radiofrequency control 186 to direct power to the RF electrode.

In some embodiments, an apparatus for advancing an intravascular device through a severe obstruction in a blood vessel is provided. The apparatus comprises a catheter having proximal and distal ends and a tip at the distal end; ultrasound emitting and receiving means mounted to the tip for transmitting ultrasound pulses and receiving echoes; an ablation means mounted to the tip; the catheter having sufficient torsional stiffness and longitudinal flexibility to enable it to be manually advanced through, and its distal end controllably rotated within, the artery solely by manual rotation of the proximal portion of the catheter; angle encoding means associated with the proximal end of the catheter for detecting changes in the angular position of the catheter; electronic means associated with the angle encoding means and transducer for generating and transmitting an electrical signal to the transducer solely in response to rotation of the catheter; means for processing echo signals to generate a graphic image of the vessel; and manually triggerable means for generating and transmitting radiofrequency energy to the ablation electrode.

In some instances, the apparatus further comprises circuitry or software for causing the image to fade after a predetermined time has elapsed. In some instances, the apparatus further comprises, in combination, a guiding sheath adapted to contain the catheter and to permit rotation and longitudinal movement of the catheter within the sheath. In some instances, the apparatus further comprises a guidewire lumen extending through the catheter from a location proximal the distal end to and through the distal tip. In some embodiments, the guidewire lumen extends to the proximal end of the catheter, the catheter having a fitting at the proximal end in communication with the guidewire lumen to enable debris produced during ablation to flow out of the patient through the lumen. In some instances, the ultrasound emitting and receiving means comprises an ultrasound transducer oriented at an angle to the longitudinal axis of the catheter so that an ultrasound beam, when rotated, will define a distally divergent conical pattern. In some instances, the apparatus further comprises circuitry or software for varying the appearance of the image to distinguish between the relative axial locations of portions of the image. In some instances, the apparatus further comprises circuitry or software for synchronizing the transmission of radiofrequency energy to the ablation electrode with the refractory period of the electrical rhythm of a patient's heart.

In some instances, the ultrasound emitting and receiving means comprises an ultrasound transducer, the ablation means comprises an ablation antenna, and the ultrasound transducer and the ablation antenna are located on opposite sides of the distal tip. In some instances, the angle encoding means comprises an encoder wheel having alternating segments that are opaque or transmissive to light; the encoder wheel being operatively associated with a proximal region of the catheter shaft for rotation in unison with the catheter shaft; a light source on one side of the wheel and a light detector on the other side of the wheel in alignment with the light source whereby the light detector may be exposed to a series of light pulses as the catheter shaft is rotated. In some instances, the angle encoding means comprises: a housing, a carrier tube rotatably mounted to the housing, the carrier tube having a lumen adapted to receive a portion of the catheter; and an angle detector contained within the housing and responsive to rotation of the carrier tube whereby the angular position of the carrier tube relative to the housing can be determined. In some embodiments, the angle encoding means comprises one of an optical encoder, an electrical encoder, and a mechanical encoder.

In some instances, the apparatus further comprises a knob attached to at least one of the ends of the carrier tube and being rotatable therewith, where the housing and knob are dimensioned to enable an operator to hold a housing in one hand while rotating the knob between the thumb and fingers of that hand. In some instances, the apparatus further comprises a tip having a longitudinal axis and the ablation electrode being disposed on one side of the tip and adapted to ablate a cavity in the occlusion substantially transversely away from the axis of the catheter and the opposite side of the tip being contoured to define a guiding surface adapted to urge the tip into the cavity in response to axial advancement of the catheter. In some embodiments, the contoured guiding surface is rounded and is approximately semicircular in transverse cross-section. In some instances, the ablation means comprises an ablation electrode and wherein the ablation electrode is relatively flat and has a width that is at least approximately half the width of the tip. In some instances, the electrical pathway between each of the ablation means and ultrasound emitting and receiving means are devoid of rotatable sliding electrical contacts or magnetically coupled electrical contacts between the catheter and the circuitry. In some instances, the catheter includes a tubular wire mesh within the wall of the catheter to enhance the torsional stiffness of the catheter, where at least one of the wires in the mesh comprises an electrical conductor for communication of electrical signals between the distal tip and the circuitry associated with at least one of the ultrasound emitting and receiving means and ablation means.

From the foregoing, it will be appreciated that the invention provides a low-cost catheter and system for intravascular ultrasound imaging and the combination of such low-cost imaging catheters with ablation means by which severe occlusions may be crossed. In some instances, however, it may be desirable to utilize only the intravascular ultrasound imaging characteristics of the invention and, to that end, devices and systems may omit the ablation electrodes and systems. The enhanced simplicity of the devices and systems enable the devices to be adapted better adapted for one-time, disposable use.

It should be understood that the foregoing description of the various aspects of the invention are intended merely to be illustrative thereof and that other embodiments, modifications and equivalents may be apparent to those skilled in the art without departing from its principles.

Having thus described the invention, what we desire to claim and secure by Letters Patent is:

1. An apparatus for advancing an intravascular device through a severe obstruction in a blood vessel comprising:
    a catheter having proximal and distal ends and a tip at the distal end;
    an ultrasound transducer mounted to the tip and configured to transmit ultrasound pulses and receive echoes;
    a radiofrequency ablation electrode mounted to the tip;
    the catheter having sufficient torsional stiffness and longitudinal flexibility to enable it to be manually advanced through, and its distal end controllably rotated within, the blood vessel by manual rotation of the proximal portion of the catheter;
    an angle encoder connected to the catheter and configured to detect changes in the angular position of the catheter;
    circuitry and software operatively associated with the angle encoder and the transducer and configured to generate and transmit an electrical signal to the transducer to activate the transducer only in response to detection of changes in the angular position of the catheter;
    circuitry and software configured to receive echo signals and to process the echo signals to create and display an image of the vessel;
    the catheter structurally arranged to be rotatable and movable solely under manual control and structurally arranged to be rotatable selectively and reversibly in clockwise or counterclockwise directions;
    manually actuable circuitry for generating and transmitting radiofrequency energy to the ablation electrode;
    wherein the apparatus is structurally arranged such that the distal tip of the catheter is positionable, rotatable, and actuatable to ablate the obstruction entirely under manual control.

2. An apparatus as defined in claim 1 further comprising circuitry or software for displaying the image for a predetermined limited time.

3. An apparatus as defined in claim 2, further comprising circuitry or software for causing the image to fade after said predetermined time has elapsed.

4. An apparatus as defined in claim 1 further comprising, in combination, a guiding sheath adapted to contain the catheter and to permit rotation and longitudinal movement of the catheter within the sheath.

5. An apparatus as defined in claim 1 further comprising a guidewire lumen extending through the catheter from a location proximal the distal end to and through the distal tip.

6. An apparatus as defined in claim 5 wherein the guidewire lumen extends to the proximal end of the catheter, the catheter having a fitting at the proximal end in communication with the guidewire lumen to enable debris produced during ablation to flow out of the patient through the lumen.

7. An apparatus as defined in claim 1 wherein the ultrasound transducer is oriented at an angle to the longitudinal axis of the catheter so that an ultrasound beam, when rotated, will define a distally divergent conical pattern.

8. An apparatus as defined in claim 7 further comprising circuitry or software for varying the appearance of the image to distinguish between the relative axial locations of portions of the image.

9. An apparatus as defined in claim 1 further comprising circuitry or software for synchronizing the transmission of radiofrequency energy to the ablation electrode with the refractory period of the electrical rhythm of a patient's heart.

10. An apparatus as defined in claim 1 wherein the ultrasound transducer and the antenna are located on the same side of the distal tip.

11. An apparatus as defined in claim 1 wherein the ultrasound transducer and ablation electrode are located on opposite sides of the distal tip.

12. An apparatus as defined in claim 1 wherein the angle encoder comprises:
   an encoder wheel having alternating segments that are opaque or transmissive to light;
   the encoder wheel being operatively associated with a proximal region of the catheter shaft for rotation in unison with the catheter shaft;
   a light source on one side of the wheel and a light detector on the other side of the wheel in alignment with the light source whereby the light detector may be exposed to a series of light pulses as the catheter shaft is rotated.

13. An apparatus as defined in claim 12 wherein the catheter shaft is detachably connected to the encoder.

14. An apparatus as defined in claim 12 wherein the angle encoder and catheter shaft are integrally connected.

15. An apparatus as defined in claim 1 wherein the angle encoder comprises:
   a housing;
   a carrier tube rotatably mounted to the housing, the carrier tube having a lumen adapted to receive a portion of the catheter;
   an angle detector contained within the housing and responsive to rotation of the carrier tube whereby the angular position of the carrier tube relative to the housing can be determined.

16. An apparatus as defined in claim 15 wherein the angle encoder comprises one of an optical encoder, an electrical encoder and a mechanical encoder.

17. An apparatus as defined in claim 16 further comprising:
   a knob attached to at least one of the ends of the carrier tube and being rotatable therewith, the housing and knob being dimensioned to enable an operator to hold a housing in one hand while rotating the knob between the thumb and fingers of that hand.

18. An apparatus as defined in claim 1 wherein the angle encoder includes
   a rotatable wheel having a radial slot receptive to a proximal portion of the catheter to engage the catheter to rotate in unison with the wheel; and
   the wheel being rotatably coupled to an encoder module for generating electrical signals corresponding to the angle of rotation of the catheter secured within the slot.

19. An apparatus as defined in claim 1 further comprising:
   the tip having a longitudinal axis and the ablation electrode being disposed on one side of the tip and adapted to ablate a cavity in the occlusion substantially transversely away from the axis of the catheter;
   the opposite side of the tip being contoured to define a guiding surface adapted to urge the tip into the cavity in response to axial advancement of the catheter.

20. An apparatus as defined in claim 19 wherein the contoured guiding surface is rounded and is approximately semicircular in transverse cross-section.

21. An apparatus as defined in claim 20 wherein the ablation electrode is relatively flat and has a width that is at least approximately half the width of the tip.

22. An apparatus as defined in claim 1 wherein the electrical pathway between each of the ablation electrode and ultrasound transducer are devoid of rotatable sliding electrical contacts or magnetically coupled electrical contacts between the catheter and the circuitry.

23. An apparatus as defined in claim 1 further comprising:
   the catheter including a tubular wire mesh within the wall of the catheter to enhance the torsional stiffness of the catheter, at least one of the wires in the mesh comprising an electrical conductor for communication of electrical signals between the distal tip and the circuitry associated with at least one of the ultrasound transducer and ablation electrode.

24. An apparatus for advancing an intravascular device through a severe obstruction in a blood vessel comprising:
   a catheter having proximal and distal ends and a tip at the distal end;
   ultrasound emitting and receiving means mounted to the tip for transmitting ultrasound pulses and receiving echoes; an ablation means mounted to the tip; the catheter having sufficient torsional stiffness and longitudinal flexibility to enable it to be manually advanced through, and its distal end controllably rotated within, the blood vessel solely by manual rotation of the proximal portion of the catheter;
   angle encoding means associated with the proximal end of the catheter for detecting changes in the angular position of the catheter;
   electronic means associated with the angle encoding means and the transducer for generating and transmitting an electrical signal to the transducer solely in response to rotation of the catheter;
   means for processing echo signals to generate a graphic image of the vessel; and
   manually triggerable means for generating and transmitting radiofrequency energy to the ablation electrode.

25. An apparatus as defined in claim 24, further comprising circuitry or software for causing the image to fade after a predetermined time has elapsed.

26. An apparatus as defined in claim 24 further comprising, in combination, a guiding sheath adapted to contain the catheter and to permit rotation and longitudinal movement of the catheter within the sheath.

27. An apparatus as defined in claim 24 further comprising a guidewire lumen extending through the catheter from a location proximal the distal end to and through the distal tip.

28. An apparatus as defined in claim 27 wherein the guidewire lumen extends to the proximal end of the catheter, the catheter having a fitting at the proximal end in communication with the guidewire lumen to enable debris produced during ablation to flow out of the patient through the lumen.

29. An apparatus as defined in claim 24 wherein the ultrasound emitting and receiving means comprises an ultrasound transducer oriented at an angle to the longitudinal axis of the catheter so that an ultrasound beam, when rotated, will define a distally divergent conical pattern.

30. An apparatus as defined in claim 29 further comprising circuitry or software for varying the appearance of the image to distinguish between the relative axial locations of portions of the image.

31. An apparatus as defined in claim 24 further comprising circuitry or software for synchronizing the transmission of radiofrequency energy to the ablation electrode with the refractory period of the electrical rhythm of a patient's heart.

32. An apparatus as defined in claim 24 wherein the ultrasound emitting and receiving means comprises an ultrasound transducer and wherein the ablation means comprises an ablation antenna and wherein the ultrasound transducer and the ablation antenna are located on opposite sides of the distal tip.

33. An apparatus as defined in claim 24 wherein the angle encoding means comprises:
   an encoder wheel having alternating segments that are opaque or transmissive to light;

the encoder wheel being operatively associated with a proximal region of the catheter shaft for rotation in unison with the catheter shaft;

a light source on one side of the wheel and a light detector on the other side of the wheel in alignment with the light source whereby the light detector may be exposed to a series of light pulses as the catheter shaft is rotated.

34. An apparatus as defined in claim 24 wherein the angle encoding means comprises:

a housing, a carrier tube rotatably mounted to the housing, the carrier tube having a lumen adapted to receive a portion of the catheter;

an angle detector contained within the housing and responsive to rotation of the carrier tube whereby the angular position of the carrier tube relative to the housing can be determined.

35. An apparatus as defined in claim 34 wherein the angle encoding means comprises one of an optical encoder, an electrical encoder and a mechanical encoder.

36. An apparatus as defined in claim 35 further comprising:

a knob attached to at least one of the ends of the carrier tube and being rotatable therewith, the housing and knob being dimensioned to enable an operator to hold a housing in one hand while rotating the knob between the thumb and fingers of that hand.

37. An apparatus as defined in claim 24 further comprising:

the tip having a longitudinal axis and the ablation electrode being disposed on one side of the tip and adapted to ablate a cavity in the occlusion substantially transversely away from the axis of the catheter;

the opposite side of the tip being contoured to define a guiding surface adapted to urge the tip into the cavity in response to axial advancement of the catheter.

38. An apparatus as defined in claim 37 wherein the contoured guiding surface is rounded and is approximately semicircular in transverse cross-section.

39. An apparatus as defined in claim 38 wherein the ablation means comprises an ablation electrode and wherein the ablation electrode is relatively flat and has a width that is at least approximately half the width of the tip.

40. An apparatus as defined in claim 24 wherein the electrical pathway between each of the ablation means and ultrasound emitting and receiving means are devoid of rotatable sliding electrical contacts or magnetically coupled electrical contacts between the catheter and the circuitry.

41. An apparatus as defined in claim 24 further comprising:

the catheter including a tubular wire mesh within the wall of the catheter to enhance the torsional stiffness of the catheter, at least one of the wires in the mesh comprising an electrical conductor for communication of electrical signals between the distal tip and the circuitry associated with at least one of the ultrasound emitting and receiving means and ablation means.

42. An apparatus for advancing through a severe obstruction in a blood vessel, comprising:

a catheter having a proximal end, a distal end, and a longitudinal axis, the catheter being configured with sufficient torsional stiffness and longitudinal flexibility to be manually advanced through the blood vessel, the proximal end having a proximal portion configured to be manipulated by a user, the distal end being controllably rotatable within the blood vessel by manual rotation of the proximal portion of the catheter, the distal end having a distal tip, the catheter comprising:

an ultrasound transducer mounted to the tip and arranged to transmit ultrasound pulses in the distal direction and receive echo signals from media in the blood vessel distal of the distal tip;

a radiofrequency ablation electrode mounted to the tip and arranged to emit radiofrequency ablation energy in the distal direction to ablate media in the blood vessel distal of the distal tip;

circuitry and software configured to receive the echo signals and configured to process the echo signals to create and display an image of the blood vessel;

manually accountable circuitry configured to generate and transmit radiofrequency energy to the ablation electrode, wherein the distal tip of the catheter can be positioned, rotated and actuated to ablate the obstruction distally of the distal tip entirely under manual control;

an angle encoder connected to the catheter and configured to detect changes in the angular position of the catheter; and circuitry and software operatively associated with the angle encoder and the ultrasound transducer and configured to generate and transmit an electrical signal to the transducer to activate the transducer only in response to detection of changes in the angular position of the catheter.

43. The apparatus of claim 42, wherein the ultrasound transducer is oriented at an oblique angle to the longitudinal axis of the catheter so that as the transducer is rotated, it emits ultrasound in a conical distally-oriented pattern.

44. The apparatus of claim 43, wherein the circuitry and software configured to display an image of the blood vessel is configured to generate an image on the display to convey to the observer a sense that the image is conical.

45. The apparatus of claim 42, wherein the ablation electrode is configured to create a void in the media at a location distal of the distal tip, the distal tip being sized to project into the void in the media created by the ablation electrode.

46. The apparatus of claim 42, wherein the RF electrode is configured to create a void offset from and in front of the catheter tip.

47. The apparatus of claim 46, wherein the distal tip comprises a wedge-like contoured surface configured to enter the void.

* * * * *